US012559792B2

(12) United States Patent
Varricchio et al.

(10) Patent No.: US 12,559,792 B2
(45) Date of Patent: Feb. 24, 2026

(54) FOOD CERTIFICATION SYSTEM

(71) Applicant: SWISSDECODE SA, Renens (CH)

(72) Inventors: Stefano Varricchio, Lausanne (CH);
Adrian Breitenmoser, Lausanne (CH);
Cylia Rochat, Chexbres (CH); **Fabien
Frery, Neuvecelle (FR); Gianpaolo
Rando**, Blonay (CH)

(73) Assignee: Swissdecode SA, Renens (CH)

( * ) Notice: Subject to any disclaimer, the term of this
patent is extended or adjusted under 35
U.S.C. 154(b) by 370 days.

(21) Appl. No.: 18/296,699

(22) Filed: Apr. 6, 2023

(65) Prior Publication Data

US 2023/0348960 A1 Nov. 2, 2023

Related U.S. Application Data

(63) Continuation of application No.
PCT/EP2021/077951, filed on Oct. 8, 2021.

(30) Foreign Application Priority Data

Oct. 9, 2020 (EP) .................................... 20201180

(51) Int. Cl.
*C12Q 1/6851* (2018.01)
*B01L 3/00* (2006.01)
*G01N 1/28* (2006.01)

(52) U.S. Cl.
CPC ...... *C12Q 1/6851* (2013.01); *B01L 3/502715*
(2013.01); *G01N 1/286* (2013.01); *B01L
2200/04* (2013.01); *B01L 2200/16* (2013.01);
*B01L 2200/18* (2013.01); *B01L 2300/023*
(2013.01); *G01N 2001/2866* (2013.01)

(58) Field of Classification Search
CPC ............. C12Q 1/6851; B01L 3/502715; B01L
2200/04; B01L 2200/16; B01L 2200/18;
B01L 2300/023; B01L 3/502; B01L 7/52;
B01L 2200/10; B01L 2200/147; B01L
2300/021; B01L 2300/0672; B01L
2300/0681; B01L 2300/123; B01L
2300/1822; B01L 2300/1827; B01L
2400/0487; B01L 2400/0611; B01L
2400/0655; B01L 3/523; B01L 3/527;
G01N 1/286; G01N 2001/2866; G01N
33/02; G01N 21/6428; G01N 21/6452;
G01N 33/48707
See application file for complete search history.

(56) References Cited

U.S. PATENT DOCUMENTS

2015/0136604 A1    5/2015    Nielsen et al.
2017/0327867 A1    11/2017   Dohale et al.
2019/0336972 A1    11/2019   Gutsell
2020/0276582 A1    9/2020    DeJohn et al.

FOREIGN PATENT DOCUMENTS

EP          3309154 A1      4/2018
WO      WO-2008148834 A1 *  12/2008   .............. A47J 31/22
WO         2011156915 A2    12/2011
WO         2011156915 A3    12/2011
WO         2015084458 A2    6/2015
WO         2015084458 A3    6/2015
WO      WO-2016124907 A1 *  8/2018    ....... G01N 35/00029
WO         2020072843 A1    4/2020

OTHER PUBLICATIONS

Medina et al., "Current Trends and Recent Advances on Food
Authenticity Technologies and Chemometric Approaches", Trends
in Food Science Technology vol. 85 pp. 163-176, Jan. 23, 2019.

* cited by examiner

*Primary Examiner* — Cynthia B Wilder
(74) *Attorney, Agent, or Firm* — Seager, Tufte &
Wickhem, LLP

(57) ABSTRACT

A food certificate system comprising a certificate generation
server, at least one reader comprising a control unit config-
ured to operate a DNA test procedure and communicate with
the certificate generation server via a global computer net-
work, and a single-use capsule insertable in the reader in a
detection position for analyzing DNA characteristics of a
food sample contained in the capsule and transmission of the
DNA measurement results to the certificate generation
server.

20 Claims, 13 Drawing Sheets

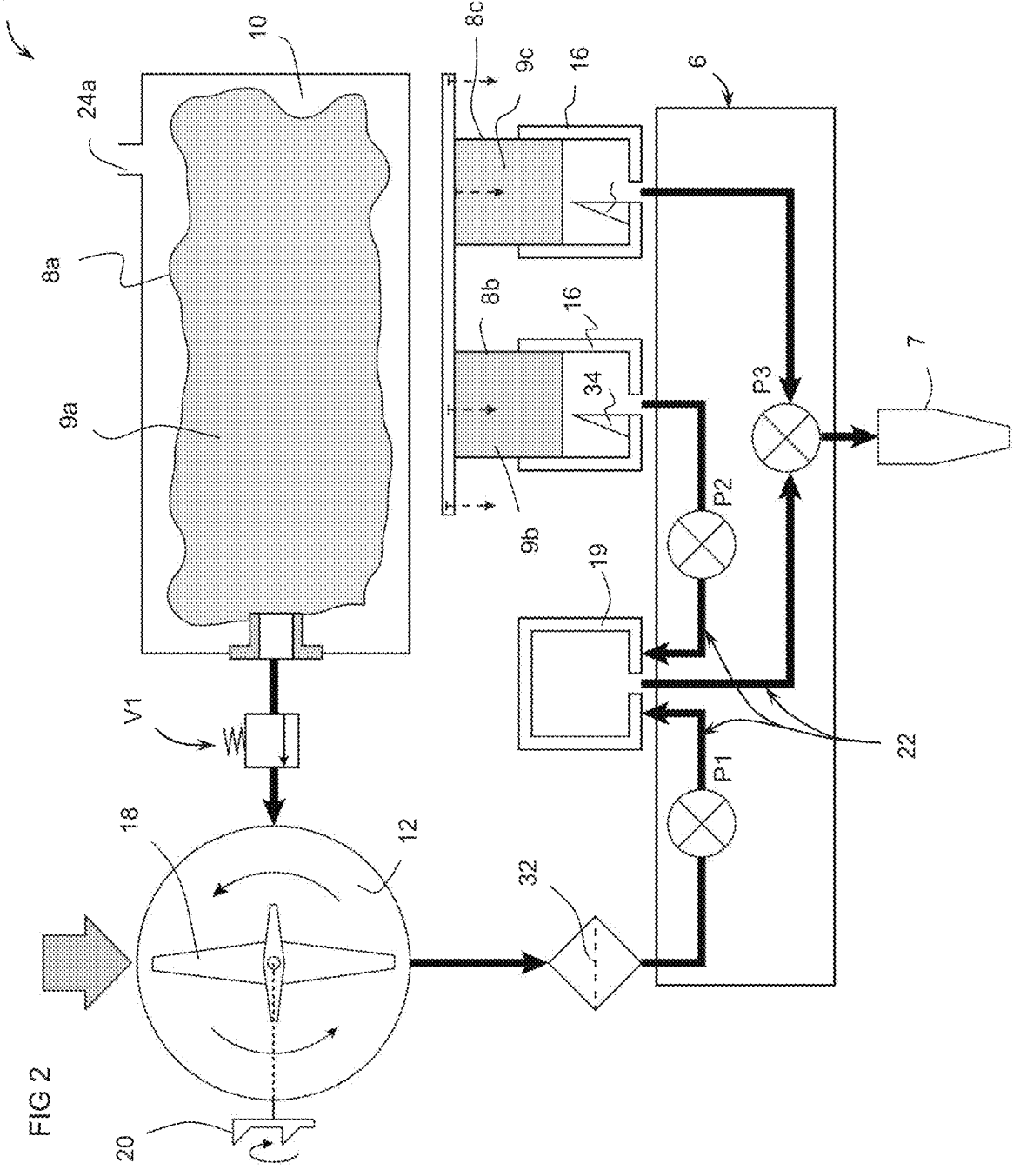

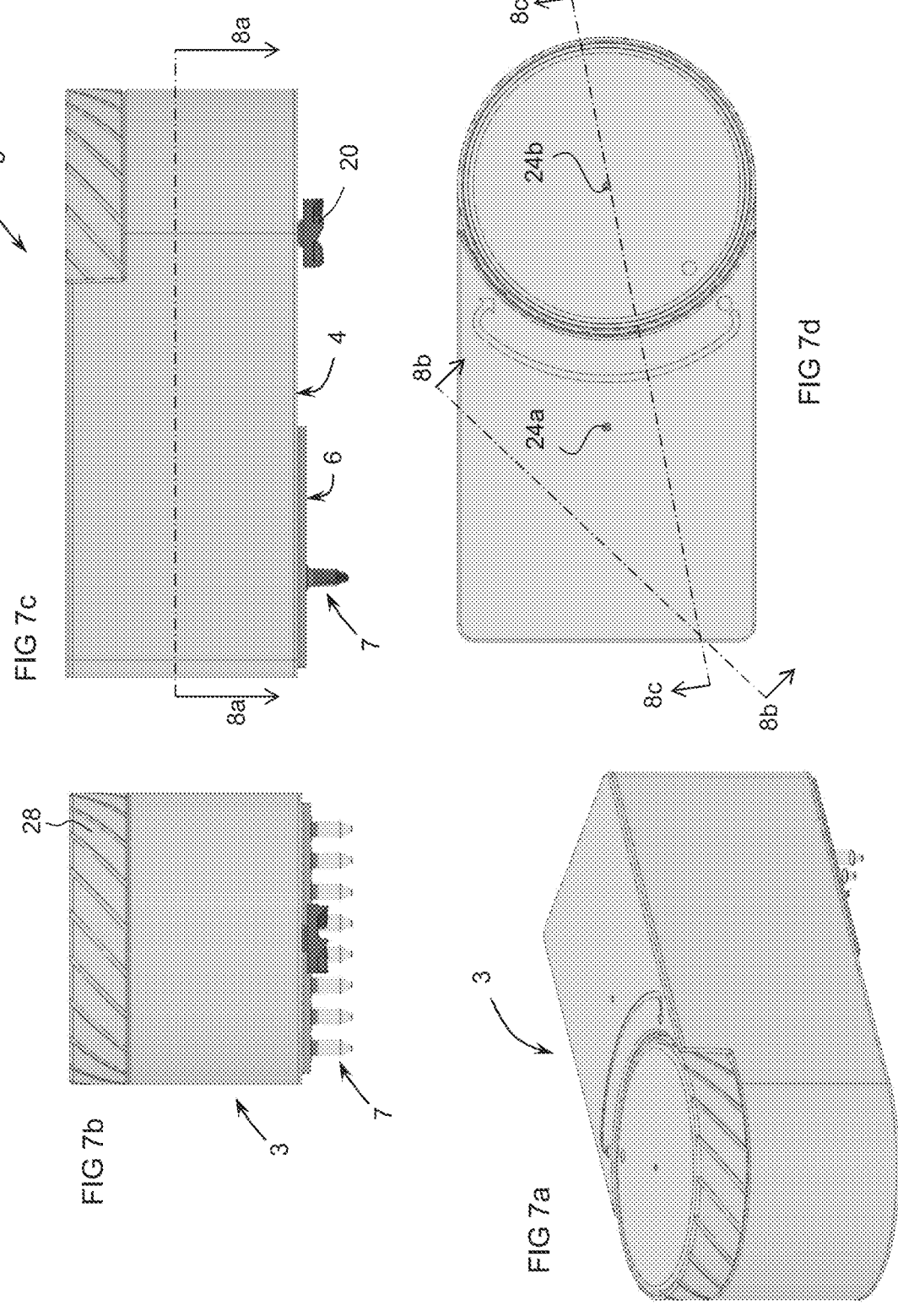

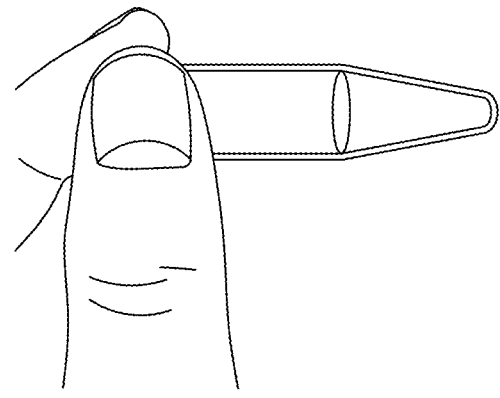
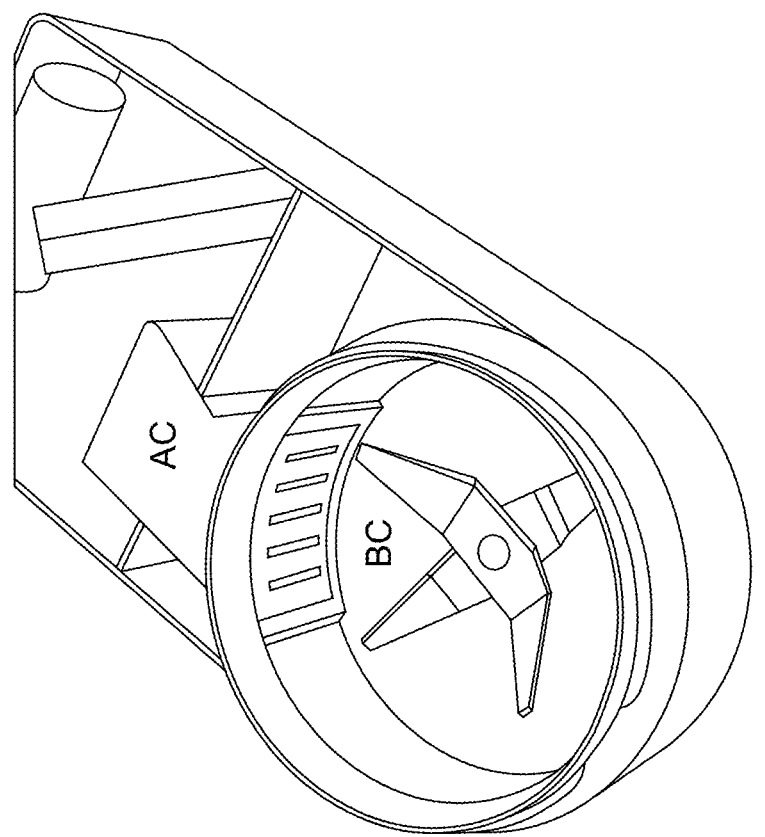
FIG. 11

FOOD CERTIFICATION SYSTEM

CROSS-REFERENCE TO RELATED APPLICATIONS

This application is a continuation of International Application No. PCT/EP2021/077951, filed Oct. 8, 2021, which claims priority to EP Application No. 20201180.5, filed Oct. 9, 2020, the contents of which are herein incorporated by reference in their entirety.

TECHNICAL FIELD

The present invention relates to a certification system for in situ DNA testing of food samples.

BACKGROUND

In conventional procedures, testing of food samples typically requires sending a sample of the food to a laboratory for DNA testing to check for certain ingredients or to certify that the food does not contain certain substances or is of a certain type, quality or origin. For instance, in certain applications there is a desire to verify the variety of a certain plant material, such as the variety of rice, or the presence of food stuffs in a food sample for instance the presence of pork in meat products. DNA testing allows to identify varieties and compositions, or the absence or presence of certain substances, however the time required to obtain these results from a laboratory, which may take 2 to 10 days is a drawback. Also, the need to send the food samples to specialized laboratories depending on the type of substances to be tested is an inconvenience and strongly limits the widespread use of such testing methods. There would therefore be need for testing of food samples in situ, close to points of production, manufacturing, processing or sale. There is also in certain applications a need to enable reliable verification or certification of the substance to be tested, avoiding manipulation and falsification of test results. Portable DNA testing equipment is becoming commercially available, however, to obtain a certificate of analysis that enables the free movement of certified food products within the value chain, the use of such portable equipment is still confined to ISO accredited laboratories.

In view of the foregoing, an object of the invention is to provide a food certification system, and a single use capsule therefor, based on DNA testing of samples that may be performed easily in various locations, producing test results rapidly and in a reliable manner.

It is advantageous to provide a food certification system that is versatile and allows rapid testing of various substances.

It is advantageous to provide a food certification system that can be performed economically and repeatedly at different sites remote from a laboratory, yet that can discriminate in an accurate and reliable manner.

Objects of the invention have been achieved by providing a single use capsule for nucleic acid testing of a food sample according to claim 1.

Objects of the invention have been achieved by providing a food certification system according to claim 15.

Objects of the invention have been achieved by providing a method of testing a food sample according to claim 18.

SUMMARY

According to a first aspect, disclosed herein is a single-use capsule for nucleic acid testing of a food sample, the capsule comprising a housing, a homogenizing chamber in the housing for receiving a food sample, a blender within the homogenizing chamber, one or more reagent containers mounted in the housing, the one or more reagent containers containing reagents for a DNA amplification process. The reagents may be hermetically sealed in the one or more reagent containers prior to use of the capsule.

Preferably, the homogenizing chamber is configured to accommodate at least 5 g, preferably at least 15 g and more preferably at least 25 g of the food sample. Preferably, the homogenizing chamber is configured to accommodate at most 100 g, preferably at most 150 g and more preferably at most 200 g of the food sample. Alternatively or additionally, the homogenizing chamber has a volume of not less than 5 $cm^3$, preferably not less than 15 $cm^3$ and more preferably not less than 25 $cm^3$. Preferably, the homogenizing chamber has a volume of not more than 100 $cm^3$, preferably not more than 150 $cm^3$ and more preferably not more than 200 $cm^3$. Accordingly, the food sample may be provided to the homogenizing chamber in an appropriate amount which enables a timely and reliable certification procedure, preferably without any further pre-processing to the food sample.

Preferably, the capsule further comprises a fluid distribution base having one or more liquid pumps. The fluid distribution base may comprise pneumatic inlets couplable sealingly to pneumatic outlets of a reader for operation of the one or more liquid pumps. The fluid distribution base preferably is coupled to the housing for mixing and distributing the reagents and extracts of the food sample.

The one or more liquid pumps may be one or more peristaltic pumps or one or more membrane pumps.

Preferably, the capsule further comprises one or more reaction chambers. The one or more reaction chambers may be coupled to the fluid distribution base in an irremovable manner.

In an advantageous embodiment, the fluid distribution base comprises liquid pumps and fluid circuits therein for transport of the liquid into the reaction chambers, which are preferably formed by test tubes, the fluid distribution base having pneumatic inlets couplable sealingly to pneumatic outlets of a reader for operation of the liquid pumps.

In an advantageous embodiment, the reagents contained within the capsule include a lyophilized substance within the reaction chamber(s) (e.g. test tube(s)) configured for producing a master-mix for specific DNA amplification. Preferably, the substance comprises an enzyme such as Bst DNA polymerase, GspM DNA polymerase and Phi29 DNA polymerase. More preferably, the reaction chambers (e.g., the test tubes) contain one or more primer and one or more enzymes for amplifying a target DNA via PCR or isothermal amplification.

Preferably, the substance for producing a master-mix for specific DNA amplification is resistant to at least one PCR inhibitor that presents in the food sample such that, with the capsule used, no washing step for removing the at least one PCR inhibitor is required when performing the test of the food sample. Accordingly, no washing chamber is needed in the entire system (e.g. the capsule or the reader).

In an advantageous embodiment, the reagents include a lysis buffer within a storage chamber of the capsule. The lysis buffer preferably is contained within a flexible pouch arranged in the storage chamber, the flexible pouch preferably forming one of the reagent containers. Preferably, the storage chamber is connected via an inlet for coupling to a pneumatic releasing system of a reader configured for producing controlled pressure in the chamber for controlled release of lysis buffer with homogenized food sample in the homogenization chamber. The storage chamber may be fluidly connected to an inlet through which a fluid for increasing the pressure in the storage chamber may be introduced for releasing the lysis buffer (e.g., into the homogenization chamber). The fluid for increasing the pressure in the storage chamber may be provided by the reader. For this purpose the inlet may be sealingly coupled to a respective outlet of the reader, e.g. to a pneumatic outlet of the reader.

In an advantageous embodiment, the lysis buffer pouch is connected to a valve allowing release of lysis buffer upon attending a threshold pressure and preventing release below said threshold pressure.

In an advantageous embodiment, the reagents contained within the capsule further include a neutralization buffer and/or a resuspension buffer.

The homogenization chamber may comprise a one-way valve for releasing gas (e.g. air) contained therein when the homogenization chamber is being filled (e.g., with lysis buffer). The one-way valve may prevent surrounding air and/or impurities from entering into the homogenization chamber once processing of the sample in the capsule has begun. The one-way valve may be provided in a lid of the capsule and/or the homogenization chamber (which is described in more detail below).

For the purpose of reliably issuing a certificate, preferably the user (e.g. a customer) and/or the environment (e.g. a customer location at which the certification machine is installed, including the reader in which the capsule is arranged) may have no influence on the food sample after the sample has been inserted into the capsule (and at least until the certificate is issued). In other words, the food sample is preferably isolated in the capsule from the external environment, the user, and/or the reader from the time it is inserted into the capsule.

As such, the nucleic acid testing of the food sample may be performed autonomously by a system comprising the capsule and the reader. After insertion into the capsule, the food sample preferably is contained therein during the testing (i.e., until all steps of the nucleic acid testing required for issuing the certificate have been completed). Preferably, after insertion of the food sample into the capsule, no manual processing and/or testing steps are required in order to complete the nucleic acid testing. The capsule and reader system may thus perform all steps from sample to result within the capsule.

Preferably, no exchange of sample between the capsule and the reader is required for performing the nucleic acid testing. In this manner, a cross-contamination between different samples via the reader can be avoided.

Preferably, the capsule is configured such that no liquid must be added from outside the capsule into the capsule, e.g. via the reader or the user. The capsule may thus be self-contained.

Preferably, no pre-processing of the food sample is required before inserting the sample into the capsule (such as cutting the sample into small pieces or grinding the sample).

A specific design of the capsule is helpful in this regard. For example, as mentioned above, the reaction chambers are preferably coupled to the fluid distribution base in an irremovable manner. Preferably, the fluid distribution base is coupled to the housing also in an irremovable manner. The capsule is preferably configured such that fluid (e.g. air) entering from the one or more pneumatic inlets (e.g. for driving the pumps) is isolated from the food sample throughout the testing process. Preferably, all the reagents are integrally contained within the capsule and inaccessible to an operator without destruction of the capsule.

In an advantageous embodiment, the homogenizing chamber of the capsule comprises a lid or cover comprising fixing means that are preferably irreversible without damage to the capsule once closed. The invention is not limited to this configuration. For example, the capsule may comprise a lid and an irreversible locking mechanism for the lid such that once the homogenizing chamber is closed by the lid, the lid may not be removed without destruction of the capsule. The irreversible locking mechanism may be provided on the lid, on the remaining part of the capsule, or both. The irreversible locking mechanism may comprise, e.g., a snap-fit.

In an advantageous embodiment, the capsule comprises one or more perforators configured to perforate one or more of said reagent containers. The capsule may further comprise a movable support. The one or more perforators may be configured to perforate said one or more reagent containers by displacement of said movable support either when the capsule is positioned in a reader by a mechanical clamping process, or by means of an automated electrical or pneumatic displacement of the movable support operated by a reader at the start of a testing procedure.

In an advantageous embodiment, the blender comprises a coupling for pluggable coupling to a complementary pluggable coupling of a motor of a reader. Preferably, the blender is configured to be rotated by the motor, i.e. a blender motor, to homogenize the food sample. Preferably, the blender comprises one or more blades, preferably the one or more blades sealingly coupled to the pluggable coupling for coupling to the complementary pluggable coupling of the motor.

Also disclosed herein according to another aspect of the invention, is a food certificate system comprising a certificate generation server, at least one reader comprising a control unit configured to operate a DNA test procedure and communicate with the certificate generation server via a global computer network, and a single-use capsule insertable in the reader in a detection position for analyzing DNA characteristics of a food sample contained in the capsule and transmission of the DNA measurement results to the certificate generation server. The single-use capsule preferably is a single-use capsule according to the first aspect described above.

The certificate generation server may be configured to generate a certificate for the sample based on the transmitted DNA measurement results, preferably in an autonomous manner. The certificate generation server may further be configured to transmit said certificate to the reader or a customer using the reader.

Preferably, the food certificate system as a whole and/or the reader and/or the capsule thereof are certified in accordance with standard ISO/IEC 17025:2017. The certificate may be a certificate compliant with standard ISO/IEC 17025:2017.

Preferably, the reader comprises a blender motor couplable to the blender of the capsule.

Preferably, the reader comprises a pneumatic circuit couplable to pneumatic inlets of the capsule, preferably to pneumatic inlets in the fluid distribution base of the capsule.

Preferably, the reader comprises a reader base and a clamping mechanism for clamping the capsule in a clamped position in which a pneumatic circuit of the reader is sealingly coupled to pneumatic inlets of the capsule and a blender motor of the reader is pluggably coupled to a blender mounted in the housing of the capsule.

Preferably, the reader includes a DNA testing system including a fluorometer measuring fluorescent light emitted by sample liquid in the one or more reaction chambers (e.g., in the one or more test tubes). More preferably, the reader includes a reader base comprising such DNA testing system including a fluorometer measuring fluorescent light emitted by sample liquid in the one or more reaction chambers (e.g., in the one or more test tubes).

Preferably, the reader base comprises a block having wells therein receiving the test tubes of the capsule therein.

Preferably, the reader base comprises heating and cooling elements for DNA amplification and/or for stopping or slowing the DNA amplification process.

Preferably, the reader comprises at least one sensor for monitoring a degree of homogeneity of the food sample in the homogenizing chamber, preferably the sensor being a torque meter or a camera, the torque meter preferably measuring a torque of the blender motor. For example, the reader and/or the certificate generation server may be configured to assess that a sufficient homogeneity of the food sample has been obtained if the torque required for turning the blender is lower than a first predetermined value. When a camera is used, the reader and/or the certificate generation server may be configured to assess that a sufficient homogeneity of the food sample has been obtained once an identified particle size is smaller than a predetermined value and/or once an identified turbidity is reached.

In an advantageous embodiment, a plurality of readers in different locations are connected to the certificate generation server.

The food certificate system preferably comprises a plurality (e.g., a fleet) of readers at different geographic locations and/or at different customers. The food certificate system may allow each customer to perform the DNA test procedure at its respective location and obtain a certificate for the food sample without having to send the food sample to a laboratory.

Also disclosed herein according to yet another aspect of the invention, is a method of testing a food sample using a system as provided above, wherein the certificate generation server controls the operation of the reader remotely, the reader performing an automated testing process without the intervention from an operator once the capsule is inserted in the reader and the testing process started.

Preferably, the method of performing DNA testing of food samples and issuance of a certificate, comprises the steps of inserting a food sample in a homogenizing chamber of a capsule, isolating the food sample into the capsule, inserting the capsule in a reader, starting the DNA testing procedure and transmission of the measurement results from the reader to a remote certificate generation server via a global computer network.

In an advantageous embodiment, the testing procedure, transmission of results and analysis are controlled by the remote server.

Preferably, the method comprises issuing a certificate compliant with standard ISO/IEC 17025:2017.

BRIEF DESCRIPTION OF THE DRAWINGS

Further objects and advantageous features of the invention will be apparent from the claims, from the detailed description, and annexed drawings, in which:

FIG. 2 is a schematic diagram of a capsule of a food certification system according to an embodiment of the invention;

FIGS. 7*a* to 7*e* are perspective, front, side, top and bottom views of a capsule of a food certification system according to an embodiment of the invention;

FIG. 8*a* is a cross-sectional view through line 8*a*-8*a* of FIG. 7*c;*

FIGS. 9 to 12 illustrate examples of use of a capsule in a food certification process according to an embodiment of the invention, whereby in this specific example a vegan sausage is tested for pork content;

DETAILED DESCRIPTION

Figure 1:
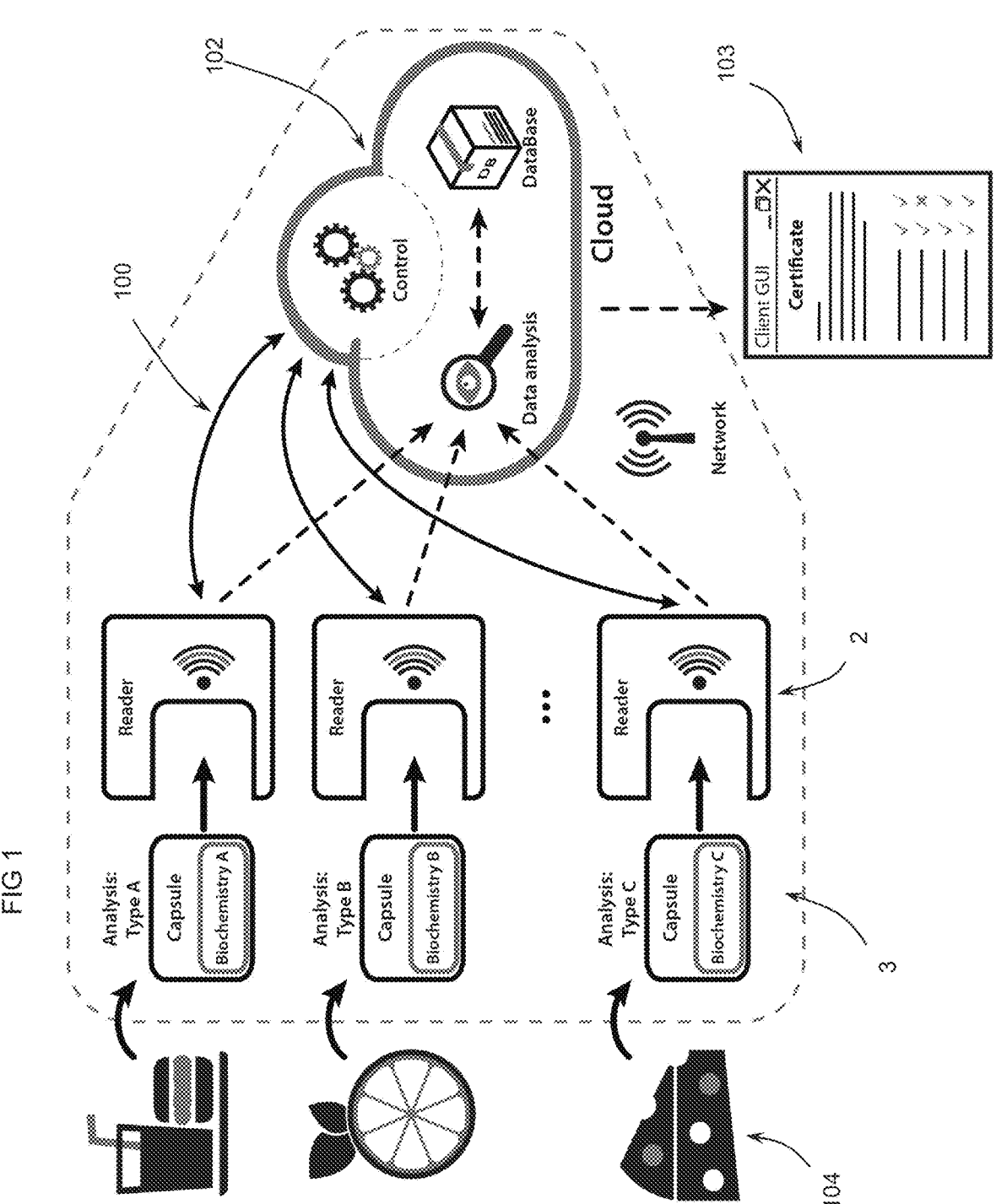
FIG. 1 is a schematic overview illustration of a food certification system according to an embodiment of the invention.
Figures 3, 4:
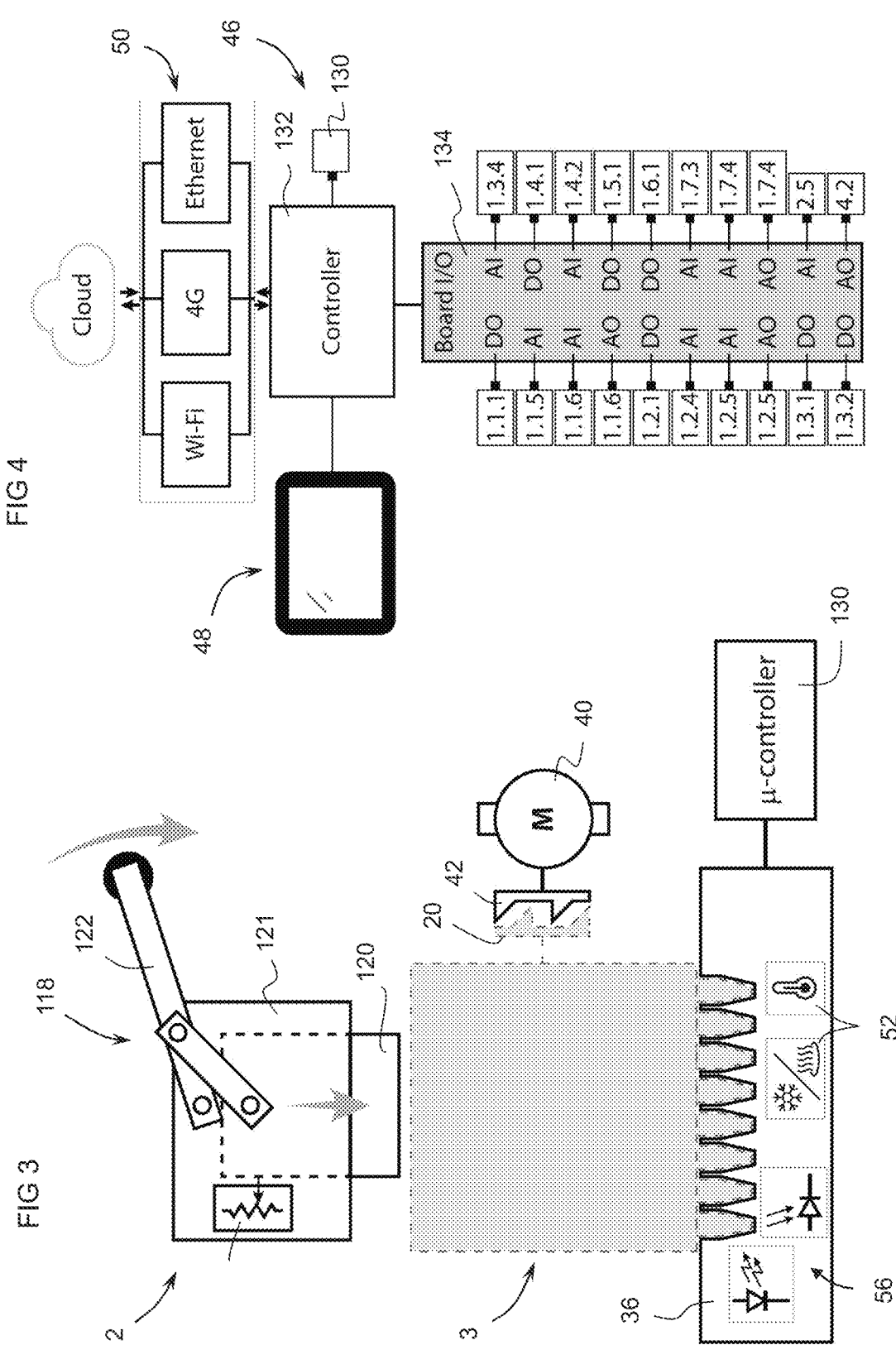
FIG. 3 is a schematic diagram of a food certification system capsule and reader according to an embodiment of the invention.
FIG. 4 is a schematic diagram of a control system of a reader of a food certification system according to an embodiment of the invention.

Referring to the figures, starting with FIG. 1, a food certification system 1 comprises a reader 2 that may be connected via a global computer network such as the internet 100 to a certificate generation server 102 for issuing certificates 103 authenticating or validating certain properties of a food sample 104 being tested. The food certification system further comprises a capsule 3 in which the food sample 104 is inserted prior to the testing process.

The sample 104 may be of various types, whether processed foods, or unprocessed plant or animal material or semi-processed plant or animal material, in solid dry or wet forms, semi-solid forms, or liquid forms.

The capsule 3 comprises a housing 4 coupled to or integrating a fluid distribution base 6 to which one or more detection tubes 7 are mounted. A plurality of reagent containers 8 are mounted within chambers of the housing, the reagent containers containing different reagents 9, 9*a*, 9*b*, 9*c* used in the food sample DNA testing process.

The capsule further comprises a blender 5 with rotatable blades 18. The blades 18 are preferably rotatable and/or pivotal. The blades are preferably sealingly coupled to a pluggable coupling 20 accessible from an outside of the capsule configured for coupling to a complementary pluggable coupling on the reader 2 connected to a motor for driving the blender blades. In particular, the blades 18 may be coupled to the pluggable coupling 20 via a mechanical connection, such as a shaft.

The blender blades are positioned within a homogenization chamber 12 of the housing. A side of the homogenization chamber 12 opposite the blades 18 is covered by a lid 28 separated from the main portion of the housing prior to positioning a sample of food within the homogenization chamber 12. Once a food sample is positioned within the homogenization chamber 12, the lid may preferably be sealingly and irreversibly closed to the housing such that once the food sample is positioned within the homogenization chamber and the lid is closed, it may no longer be removed without destruction of the capsule. Various per se known mechanisms such as hooks or ratchet teeth that can advance one direction and get caught in the opposite direction may be used for the irreversible locking mechanism.

In a variant, it is possible to have a removable lid.

However, for ensuring reliable food certification process once the food sample is positioned within the capsule, the cover is preferably not removable without destruction of the capsule such that the sample inserted within the capsule is effectively the sample being tested and for which a certificate 104 is issued. In other words, the correct chain of custody should be guaranteed.

The housing further comprises a storage chamber 10 for a first reagent that may in particular comprise a lysis buffer for mixing with the food sample for the DNA extraction process. The lysis storage chamber is coupled to the homogenization chamber via a valve V1 which may, for instance be in the form of a duckbill valve that opens under a specified pressure for transferring lysis buffer 9a from the reagent storage chamber 10 to the homogenization chamber 12. The lysis buffer may advantageously be contained in a hermetically sealed pouch 8a comprising a flexible membrane containing the lysis 9a that collapses as the lysis buffer is consumed, preferably without letting air enter into the pouch containing the lysis buffer. The first reagent storage chamber 10 comprising the lysis buffer is coupled to a pneumatic inlet 24a but couples sealingly to a pneumatic outlet in the reader 2 for applying pressure within the storage chamber 10 when required to transfer lysis buffer into the homogenization chamber.

The homogenization chamber is also coupled via a pneumatic inlet 24b, for instance on a top portion such as through the cover 28, that is sealingly coupled to a pressure outlet of the reader 2 when the capsule 3 is mounted in the reader to transfer homogenized lysis buffer and food sample out of the homogenization chamber 12 and into the fluid distribution base 6. Alternatively or additionally, the inlet 24b may serve for releasing a pressure from the homogenization chamber. In this case, the inlet 24b may be provided with a one-way valve releasing an overpressure in the homogenization chamber towards the reader and/or the surrounding atmosphere.

The homogenization chamber is fluidically coupled to the fluid distribution base via a filter 32 that retains any solid particles and allows the lysis buffer and liquid food components to be transferred fluidically into the fluid distribution base. The homogenization chamber may be fluidically coupled to the fluid distribution base via an output chamber 14, which is preferably provided downstream of the filter 32 from the homogenization chamber.

The housing advantageously comprises at least one or more further reagent storage chambers 15 containing one or more reagents. In the reagent storage chambers 15 reagent containers 8b, 8c containing reagents 9b, 9c for the testing process may be mounted. These further reagents may, for instance, include a neutralization buffer 9b and/or a suspension buffer 9a.

Preferably, the further reagents are contained in hermetically sealed containers that are perforated or opened during the testing process when the capsule 3 is placed within the reader 2.

In the illustrated embodiment, the reagent containers are positioned and held by reagent container docks 16 provided with perforators 34 whereby perforation is performed by applying pressure on a movable support 17. Pressure may be applied on the movable support 17 mechanically by a lever or rod (not shown) pressed into the housing 4 when it is inserted in the reader 2, or using a pneumatic system of the reader coupled to an inlet of the housing. In the present embodiment, the pressure supplied for displacement of the movable support 17 is gas pressure in the storage chamber 10 that also serves to apply pressure on the lysis buffer pouch 8a. Therefore, at the beginning of the testing process when lysis buffer 9a is transferred to the homogenization chamber 12 by applying pressure in the storage chamber 10, the movable support is displaced thus pressing down the reagent containers 8b, 8c on the perforators 34 and cause perforation of the reagent containers 8a, 8b. In the illustrated embodiment of FIGS. 8a-8e, the reagent containers 8a, 8b are held in the docking position prior to perforation at a first angle and as the movable support is displaced vertically the reagent containers are pivoted such that the perforators 34 pierce the bottom walls of the reagent containers. Liquid may be transferred from the reagent containers to the fluid distribution base by gravity or by pneumatic pressure or combinations thereof. The capsule, however, could also be designed in a different manner, e.g. with perforators that are movable in order to pierce the one or more reagent containers (not shown). The one or more reagent containers may then be stationary in the capsule (not shown).

Advantageously, the hermetically sealed reagents within the capsule prevent alteration of the reagents prior to use of the capsule, which may thus have a very long shelf life. The capsule may be provided with a plurality of reagents that are used for various testing protocols depending on the food substance, whereby not all of the reagents may be used in each particular process. The transfer of liquids from the reagents may be controlled by the pneumatic circuit of the reader 2. The above configuration allows one or a few capsules to be used for a broad variety of food sample tests, simplifying thus the deployment in the field.

Preferably the housing further comprises a mixing chamber 19 to which the food sample from the homogenization chamber 12 (preferably including the lysis buffer 9a from the reagent storage chamber 10) and the reagents from the one or more reagent storage chambers 15 (e.g., reagents 9b, 9c from the reagent containers 8b, 8c) may be delivered by the fluid distribution base 6. These components are mixed in the mixing chamber 19 before being further delivered to the test tubes 7.

A plurality of test tubes 7 fixedly and sealingly coupled to the fluid distribution base 6 receive the liquid samples outputted from the food distribution base 6 for reading by the reader 2. The test tubes 7 are received within corresponding lodgings or test positions within a reader base 36 of the reader 2. The reader base 36 may comprise temperature control elements 52, in particular heating and cooling elements such as resistance heaters and Peltier cooling elements as well as temperature sensors for regulating the temperature in the test tubes 7, including warming and subsequently cooling the liquid samples to be tested.

The reader further comprises a detection system 56 which in particular may include a fluorescent lighting system and a reading system for reading the DNA markers emitted by the liquid sample.

The reader 2 comprises a blender motor 40 driving a rotating coupling 42 that is a pluggably connectable to the coupling 20 of the capsule 3. The reader 2 further comprises a pneumatic circuit 44, a user interface 48, a communication module 50, and a control unit 46. The control unit controls operation of the blender motor 40 and the pneumatic circuit 44 for the testing process in which a food sample is homogenized and mixed with the lysis buffer and other reagents and transferred via the food distribution base 6 to the test tubes 7.

Within the fluid distribution base 6 are various fluid channels 22 interconnecting the capsule homogenization chamber 12 to the reagent storage chamber(s) 15, the mixing chamber 19 as well as to the test tubes 7, fluid flow being effected by pumps P1, P2, P3 and/or valves integrated in the fluid distribution base using pressure from the pumps or from the pneumatic circuit, for instance the upstream pressure on the liquid in the capsule. There are many means for transferring liquid in a fluid distribution circuit using peristaltic type of pumps or membrane pumps, for instance operated by pneumatic circuits, that may also be used for controlling valves.

Figure 5:
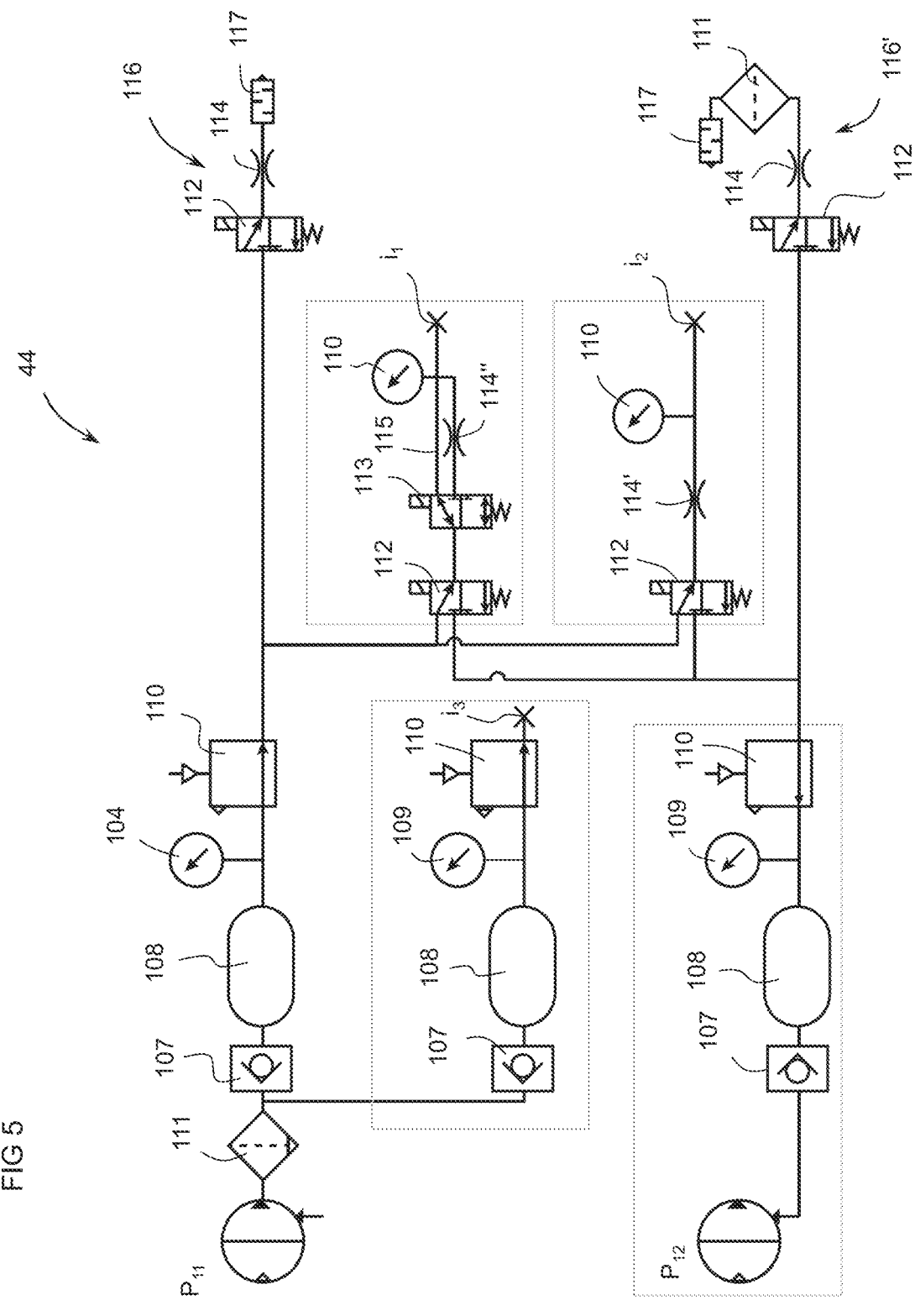
FIG. 5 is a schematic diagram of a pneumatic circuit of a reader of a food certification system according to an embodiment of the invention.

In the schematic illustration of FIG. 5 an embodiment of a pneumatic circuit of the reader is illustrated. The pneumatic circuit drives the peristaltic pumps P1, P2, P3 of the fluid distribution base 6 of the capsule 3 through rail-to-rail pneumatic outputs and corresponding pneumatic interfaces i1, i2 as well as generating pressure to control the release of the lysis buffer through a modulation of the pressure in the lysis buffer chamber 10 containing the pouch via pneumatic interface i3. The pneumatic circuit has two sources of pressure, one forming a compressed air line and one forming a vacuum line, which may comprise:

pumps P11, P12 mounted either as compressor or vacuum pump according to their use and capable to generate pressures from −0.7 bar to 3 bar, for instance diaphragm pumps;

check-valves 107 to retain pressure in the system and mounted according to their sense of operation;

reservoirs 108 to stabilize the pressure and increase the capacity of the system, allowing not to have the pumps turned on in permanence, with a volume of for instance around 1 dL;

pressure sensors 109 to monitor the residual pressure in the reservoirs, having a measurement range for instance from 0 bar to 10 bar for the compressed air circuit and from 1 bar to 0 bar for the vacuum circuit;

proportional valves 110 to electronically control the downstream pressure, for instance piezoelectric valves;

air filters 111 may be mounted at air inlets or between the pumps and the check valves.

Pressure regulators may include a closed-loop controller and a downstream pressure sensor.

The rail-to-rail pneumatic interfaces drive the pumps P1, P2, P3 embedded in the fluid distribution base. Output pressure between the compressed air and the vacuum lines may be switched with 3/2 pneumatic valves 112 (2 output states possible, "high" equal to the compressed air line and "low" equal to the vacuum line). The output pressures of all pneumatic interfaces may be independently monitored through independent pressure sensors 109.

In embodiments, there may be different types of rail-to-rail pneumatic outputs, for instance including:

x1 rail-to-rail output i1 with modular pneumatic resistance. This output i1 is meant to control the inflation and deflation of a specific valve of the fluid distribution base where the deflation must happen in about 1s, whereas the inflation must be much faster, e.g. in the range of 100 ms. This may be achieved with the use of an additional 3/2 pneumatic valve 113 that redirects the flow through a high resistance flow restrictor 114" during the phase of deflation and redirects the flow through a low resistance pipe 115 otherwise.

x12 rail-to-rail outputs i2 with fixed pneumatic resistance. In this case the fluidic resistance and therefore the flow through the valve is fixed and limited by a flow-restrictor 114' that can be manually changed to match the desired inflation/deflation speed of the valves. Each of the plurality of valves has its own flow restrictor and the behavior of all the pneumatic outputs i2 can be individually adapted.

Two pressure bleeders 116, 116' are present on both the compressed air line and the vacuum line. The pressure bleeder may comprise a 3/2 valve 112, a flow restrictor 114 and a silencer 117. The bleeder 116' for the vacuum line includes an air filter 111 not to suck dust particles into the pneumatic circuit.

The pneumatic circuit also controls the pressure in the lysis buffer storage chamber through an output interface i3 of the compressed air line which is coupled to the compressed air pump P11 via a check valve 107, air tank 108, pressure sensors 109 and proportional valves 110. The air tank 108 may be larger, for instance around 0.7 L, compared to the 0.1 L of the pressure sources for the fluid distribution base 6. Pneumatic interface i3 for the lysis chamber 10 couples to the inlet 24a of the capsule storage chamber 10.

The reader 2 comprises a clamping mechanism 118 configured to hold the capsule inside the reader during the entire run of the analysis and to guarantee that the pneumatic interfaces i1, i2, i3 couple sealingly against the corresponding capsule inlets on the fluid distribution base 6 for driving the peristaltic pumps P1, P2, P3 and on the housing 4 to inlets 24a, 24b of the chambers 10, 12. In the clamped position the blender motor couplings 20, 42 are engaged and the test tubes 7 are inserted and aligned in detection positions in the reader base 36.

The clamp mechanism may comprise for instance a piston 120 slidingly mounted in a guide block 121, movably actuated by moving a manual lever mechanism 122 or other manual or electrical actuation mechanism. The resting position of the mechanism is preferably with the piston up, kept in place for instance by a spring (not shown). When the capsule is inserted the piston is moved downwards and blocked in place by the manual lever that guarantees the stability of the mechanism. The reader comprises a position sensor 123 to monitor the position of the clamping mechanism piston throughout the whole analysis and to prevent the removal of the capsule without the consent of the operator. Force sensors may be included in the mechanism to monitor the forces applied on the capsule and guarantee that they are within the specified range for the pneumatic circuit function.

The reader base 36 may comprise a thermal cycler and/or a fluorometer configured to generate the temperature profile appropriate to each different biochemical reaction and provide a real-time readout of the DNA amplification. The reader base may for instance include:

a metal block individually surrounding each of the analysis wells receiving each a test tube therein;

an array of temperature sensors to individually monitor the temperature of each test tube;

a resistor to heat the thermoblock through the Joule effect and a heatsink connected to an array of Peltier elements to cool the thermoblock;

an array of LEDs (e.g. one for each analysis well) to excite the fluorescent signal of the biochemical reaction at the appropriate wavelength;

an array of photodiodes (e.g. one for each analysis well) and a dichroic filter to read the emitted fluorescent signal of the biochemical reaction in the emission window.

The control of the temperature profile and the acquisition of the readout may be controlled automatically with a microcontroller 130 of the control unit 46. The control unit 46 controls and monitors the functioning of the reader base 36 and further communicates with the remote certification server 102 to transfer measurement results, including metadata of the analysis, as well as the status of the reader 2. The control unit may comprise for instance a computing unit 132 in charge of running embedded software and controlling a data acquisition board 134, controlling the heatblock microcontroller 130, interpreting the user inputs through a user interface 48 for instance comprising a touchscreen, and communicating with the remote server through the communication module 50. The data-acquisition board (DAQ) 134 reads and generates the analog and digital signals that control the different elements.

The digital outputs DO are dedicated to control the diaphragm pumps P1, P2, P3, and all the pneumatic valves. The analog outputs (AO) are dedicated to the control of the proportional valves of the pneumatic circuit as well as the blender motor. The analog inputs (AI) are dedicated to the readout of the different sensors, monitoring both the pneumatic circuit and the clamp in terms of position and force applied.

The communication module 50 used to communicate bi-directionally with the remote server may for instance comprise a plurality of communication units using different transmission technologies such as 4G, Wi-Fi and Ethernet. A preferred communication method for field use is via 4G, and alternatively if the 4G is temporary not available, Wi-Fi or a fixed line network can be used.

The user interface 48 allows the operator of the reader to start the testing process and to input commands such as the type of process to be carried out, type of food sample, and batch identification information for instance.

The reader may be connected via various wireless and wired means to the global computer network 100 in order to transfer the measurement results to a remote certification server 102. The remote certification server may verify the measurement results with a database of information defining the DNA samples that are being verified and to return or emit a certificate with the measurement results. The certificate may for instance certify that a meat sample for instance contains any pork (or the contrary) or that the meat sample is 100% beef, or that a rice sample is for instance of a certain variety (e.g. Basmati), possibly also from a certain region provided that the DNA of the sample may be discriminated from other samples.

According to an embodiment of the invention, a plurality of readers 2 placed at points of analysis at different locations may be connected to one or more servers 102, whereby each reader can execute a set of analyses with the disposable and single use capsules 3. Capsules with different reagents may be provided, each corresponding to a dedicated and specific type of test. The remote server 102 may monitor and manage operation, activities and data resulting from the fleet of readers 2. The remote server may have three main subsystems: (I) a "Control" system is responsible of managing and controlling the activity of the fleet of readers during the analysis, (II) a "Database" contains the analysis protocols to execute and the results of past analysis and (III) a "Data Analysis" system contains the protocols to analyze the data from the test runs and return a result such as in the form of certificate 103 as well as providing analysis of metadata giving further insight based on "big-data" such as forecasting of outbursts of pathogens or back-tracking contaminations in the food supply chain to the source.

The capsule contains the necessary hardware and reagents to perform the entire analysis protocol. The reader contains the necessary hardware to actuate and operate the capsule according to its dedicated analysis protocol, to monitor the correct execution of the analysis protocol, to read the outcome of the analysis and to communicate with the remote certification server.

The server 102 may control the readers 2 with a master/slave scheme to provide compliance with the technical competence and quality management procedures, for instance of ISO/IEC 17025:2017 guidelines, so that measurements originating from the readers can be used to perform analyses accredited under accepted standards such as ISO/IEC 17025:2017 standards. The outcome of the analysis for the user thus may be a certificate delivered under an accepted standard such as the ISO/IEC 17025:2017 standard, as well as the metadata of each analysis performed by the system. The certification server 102 is not bound to be in the same hardware of the readers 2 but may be centralized whereas the readers 2 may form a decentralized fleet located at customer premises such as farms, collection centers, food transportation vehicles and factories, whereas the certification server may be located in a standards accredited premise, such as a ISO/IEC 17025:2017 accredited premise.

Embodiments of the present invention allow:

autonomously accepting samples within the scope of the accredited analysis, processing accepted samples, extracting analytes of interest from accepted samples, performing analysis and measurements on prepared analytes, uploading performed measurements to the certification server, analyzing the resulting measurements, performing quality controls to validate the conformity of the analysis, verifying and validating the analysis results, fulfilling data integrity requirements of sample data, raw data and analysis results, and emitting a certificate of analysis.

Figure 6:
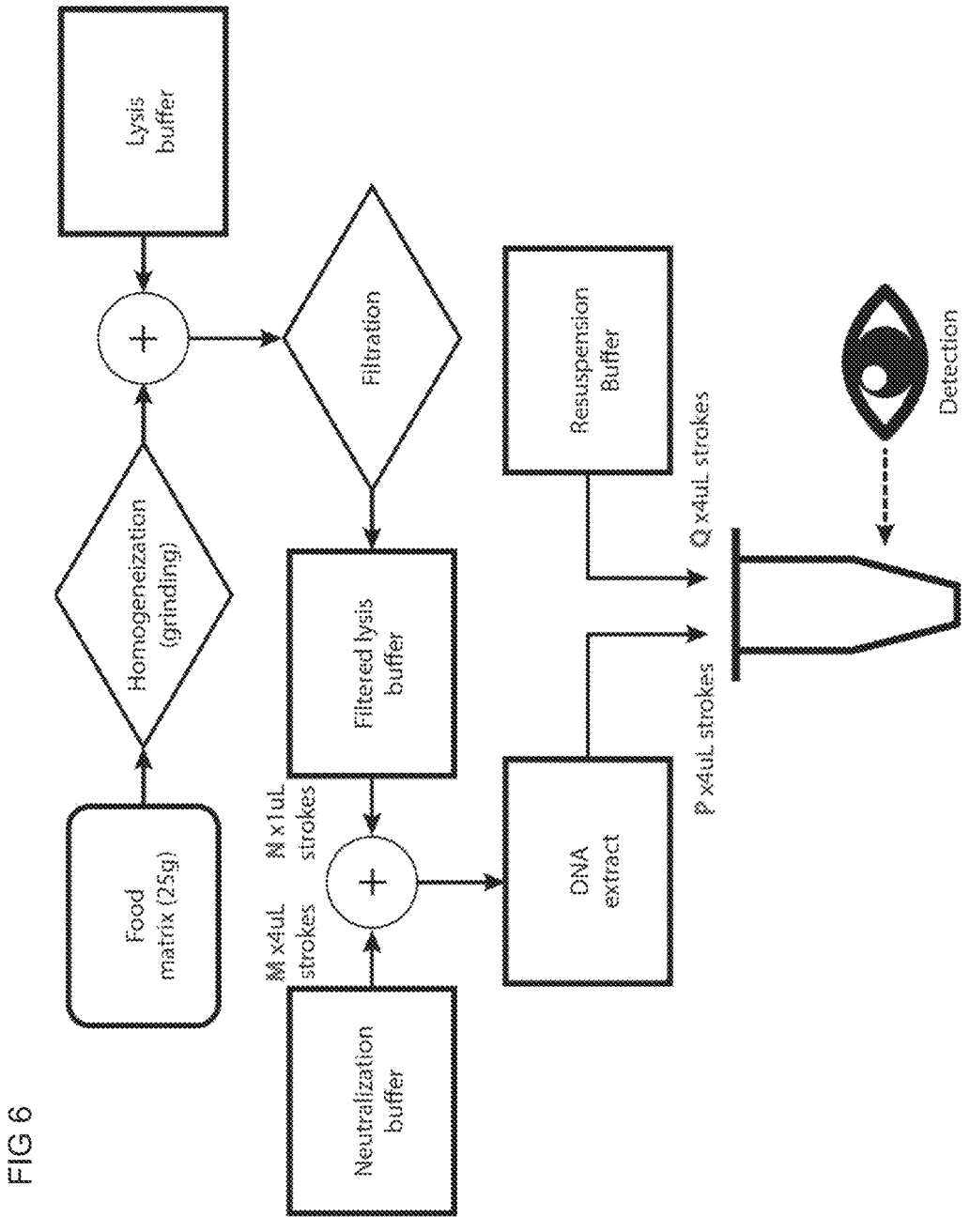
FIG. 6 is schematic block diagram of a food certification process according to an embodiment of the invention.
Figures 7E, 8A:
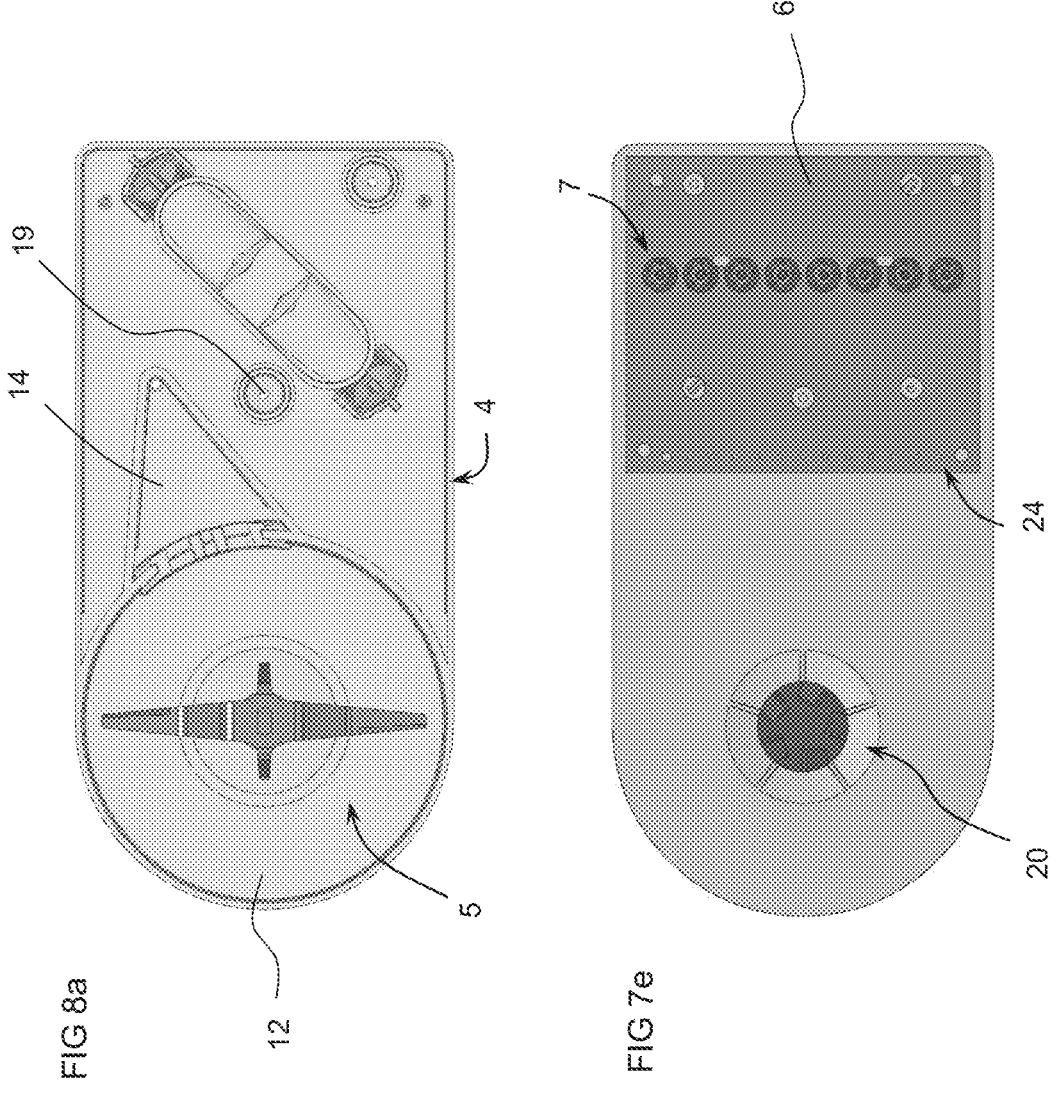
Figures 8B, 8C:
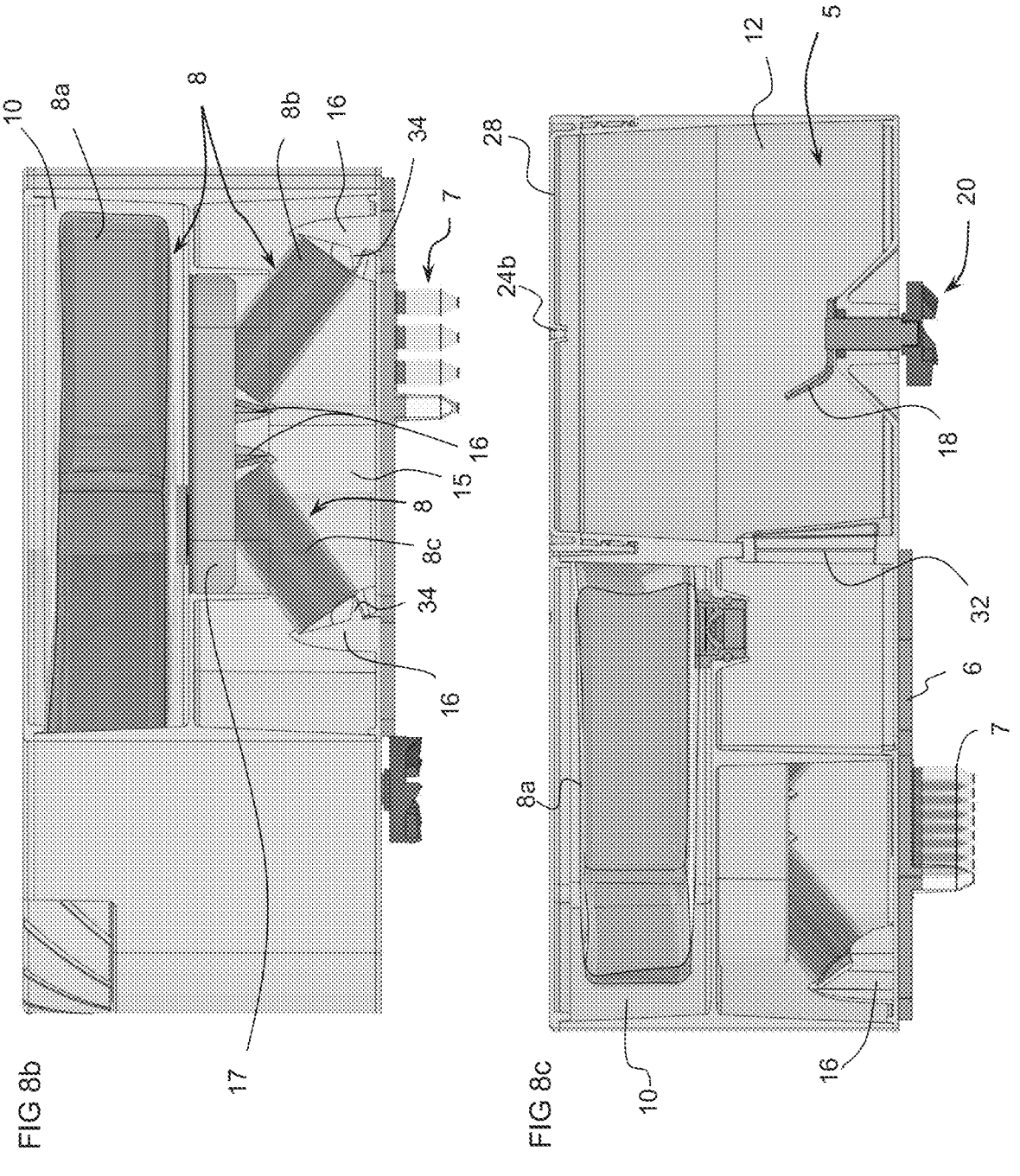
FIG. 8*b* is a cross-sectional view through line 8*b*-8*b* of FIG. 7*d;*
FIG. 8*c* is a cross-sectional view through line 8*c*-8*c* of FIG. 7*d;*
Figure 8D:
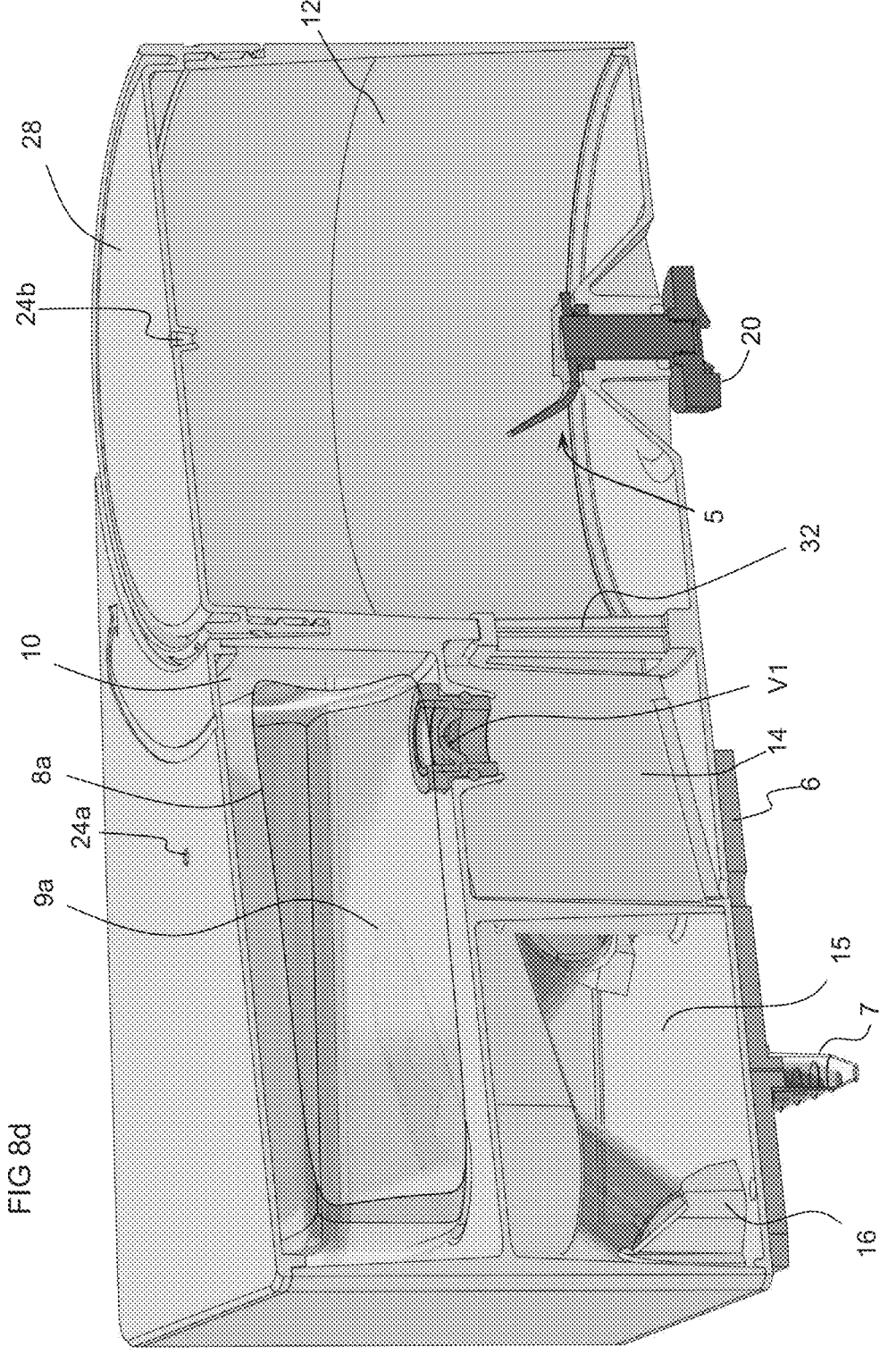
FIG. 8*d* is a perspective view of the capsule cross-section of FIG. 8*c;*

An example of an analysis protocol for generating a certificate 103 according to an embodiment of the invention is shown in FIG. 6. First, a sample of food, for instance at least 25 g of food to be tested, is inserted in the homogenization chamber 12 of a capsule 3 and the capsule is inserted in a reader 2 and clamped in position to ensure a sealed connection between the capsule inlets and pneumatic system of the reader. The blender motor is operated to homogenize the food sample in the blending chamber. A lysis buffer is then added in the blending chamber to extract the DNA from the food matrix which, after coarse filtering, results in an alkaline solution rich in DNA. To this solution is then added a neutralization buffer to obtain a pH-neutral solution. In parallel a buffer is used to resuspend a lyophilized pellet contained in the test tube and obtain a master-mix to run the DNA amplification reaction. The lyophilized pellet may contain enzymes, oligonucleotides and other molecular components necessary or useful to run the DNA amplification reaction. The pH-neutral DNA extract is added to the master-mix in the test tube and the DNA-amplification reaction is started by applying heat in the heat block of the reader base. The amount of DNA-copies generated over time is read with the fluorometer in the reader base.

The ratios and quantities of the different reagents can be optimized to different types of reactions and food matrices (as shown in FIG. 6 with the letters M,N,P,Q).

Advantageously, since the measurement results in such embodiments are preferably transmitted to a remote server for authentication and the capsule is in a sealed configuration once the food sample is placed therein and cannot be opened without destruction thereof, falsification of the measurement results is prevented and a reliable certification process is provided. Also, a very simple infield process may be used with the operator simply placing a food sample into the homogenization chamber, closing the lid and placing the capsule within the reader, subsequently starting the measurement process which may happen automatically without further intervention from the operator.

Since the capsule may contain various reagents, only some of which may be used for any particular process that the operator can select on the reader, various food types and samples may be tested with a single capsule.

Moreover, the capsule advantageously comprises a plurality of reaction chambers, for instance from 4 to 10 whereby the reaction chambers may comprise identical test reactions (replicates) or may have different test reactions depending on whether a plurality of results for the reliability is performed or whether different tests needs to be performed on the same food sample. For instance, different test tubes may be provided with different markers if a plurality of DNA tests are performed.

The test tubes may further advantageously comprise, according to embodiment of the invention, a lyophilized reagent that reacts with the liquid sample for the DNA testing process whereby different test tubes may be provided with different lyophilized substances.

Since all of the reagents and substances are integrally contained within the capsule and inaccessible to an operator without destruction of the capsule, the accredited laboratory owning the system is in full control of the analysis and therefore the certification process may be in a reliable and simple manner.

EXAMPLE 1: AUTONOMOUSLY ACCEPTING SAMPLES WITHIN THE SCOPE OF THE ACCREDITED ANALYSIS

Sample acceptance is done contractually and verified through controls along the testing procedure. At the food manufacturing site, the list of raw materials that need a certificate is disclosed to the certifying agent and specified in a service agreement. This list matches the material (matrixes) and the analytical tests the certifying agent is accredited for. For example, the certifying agent may be ISO 17025:2017 accredited to provide laboratory testing service for molecular biology analysis in the field of foodstuff. In the service agreement, the customer responsibility is to put at least 25 grams of sample to be tested (i.e. vegan sausages) in the testing capsule (e.g. see FIG. 9) and to close the capsule.

Once the capsule is closed, the certifying agent responsibility is to accept the capsule containing the sample for analysis. Usually, sample acceptance is done once a sample for analysis has reached the accredited laboratory. In the present invention, the customer is submitting a sample for analysis by inserting a closed capsule in the reader of the food certification system.

The food certification system recognizes the capsule through a QR code. Phenotypic measures in the sample chamber (e.g. impedance) and comparison of their profile against known reference profiles allows the accredited laboratory to confirm that the capsule is filled with a sample for which there is contractual and regulatory compliance with the testing service offered.

EXAMPLE 2: PROCESSING AND EXTRACTING ANALYTES OF INTEREST FROM ACCEPTED SAMPLES

Figures 9, 10:
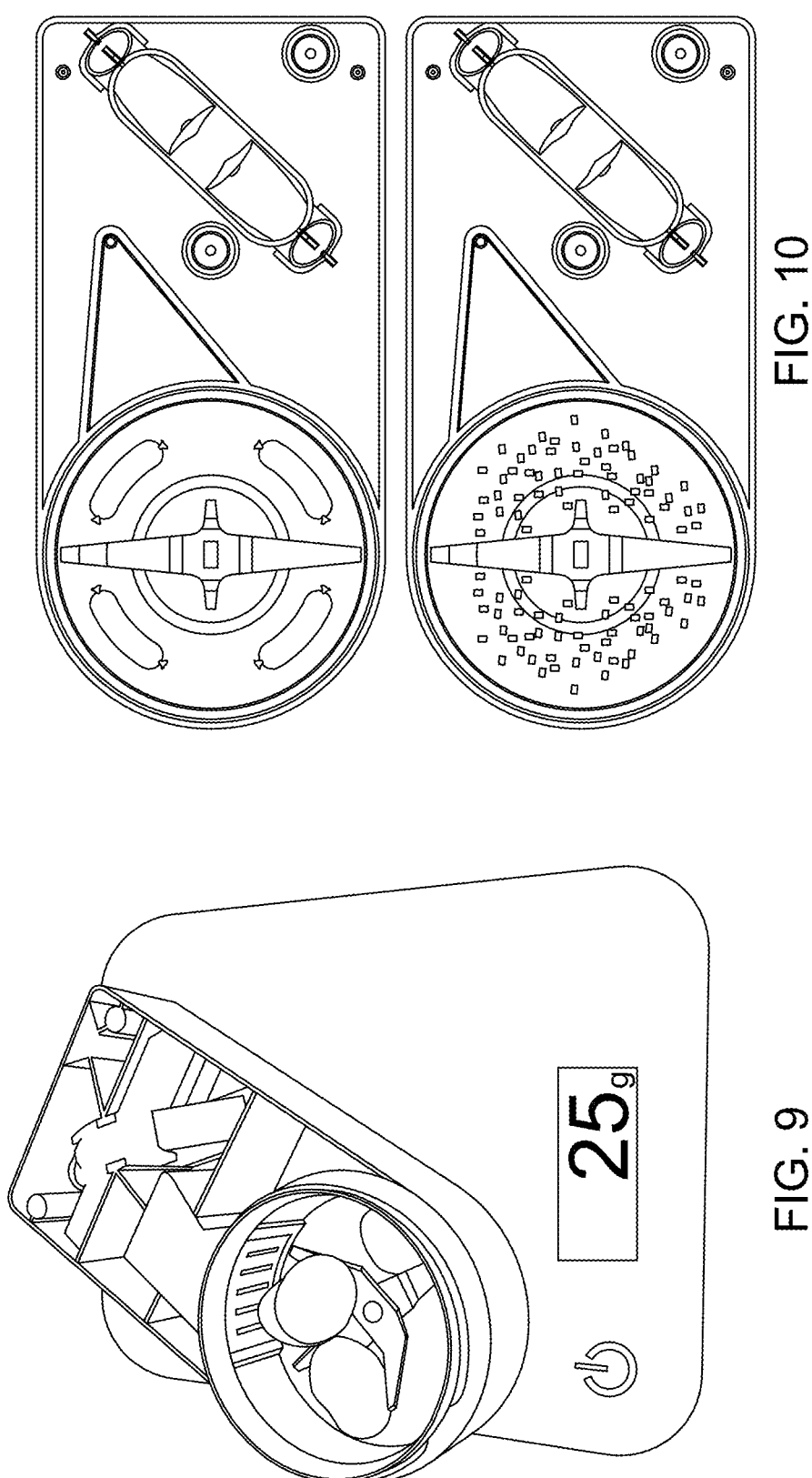

In this example, the analyte of interest (genomic DNA) is extracted from the food sample by alkaline lysis. A vegan sausage (25 grams) is homogenized with the blades of the disposable blender (FIG. 10). The lysis buffer (NaOH 100 mM) is injected into the blending chamber by actuating pressure on a lysis pouch container placed on the top of the capsule. The shearing of the blades and the alkaline conditions (pH>13) break the cells and release the DNA in the liquid extract. The blending and extraction conditions are terminated when the torque registered in the blade motor reaches plateau. In the system, this is controlled through monitoring of the electrical current fed to the motor.

EXAMPLE 3: PERFORMING ANALYSIS AND MEASUREMENTS ON THE PREPARED ANALYTE SOLUTION

The prepared analyte solution (sample lysate) is then filtered in a coarse way to remove debris. In the capsule, the filtration is obtained by forcing the sample lysate to pass from the blending chamber (BC) into the analyte chamber (AC) (FIG. 11) through a porous membrane window. The liquid is moved by the centrifugal force exercised by the blades in the blending chamber. The porous membrane can be made of nitrocellulose, PVDF, PP, nylon, CME with pores from 5 to 150 μm. The filtered liquid is exempt from debris bigger than the pore size to facilitate the downstream liquid handling.

Figure 12:
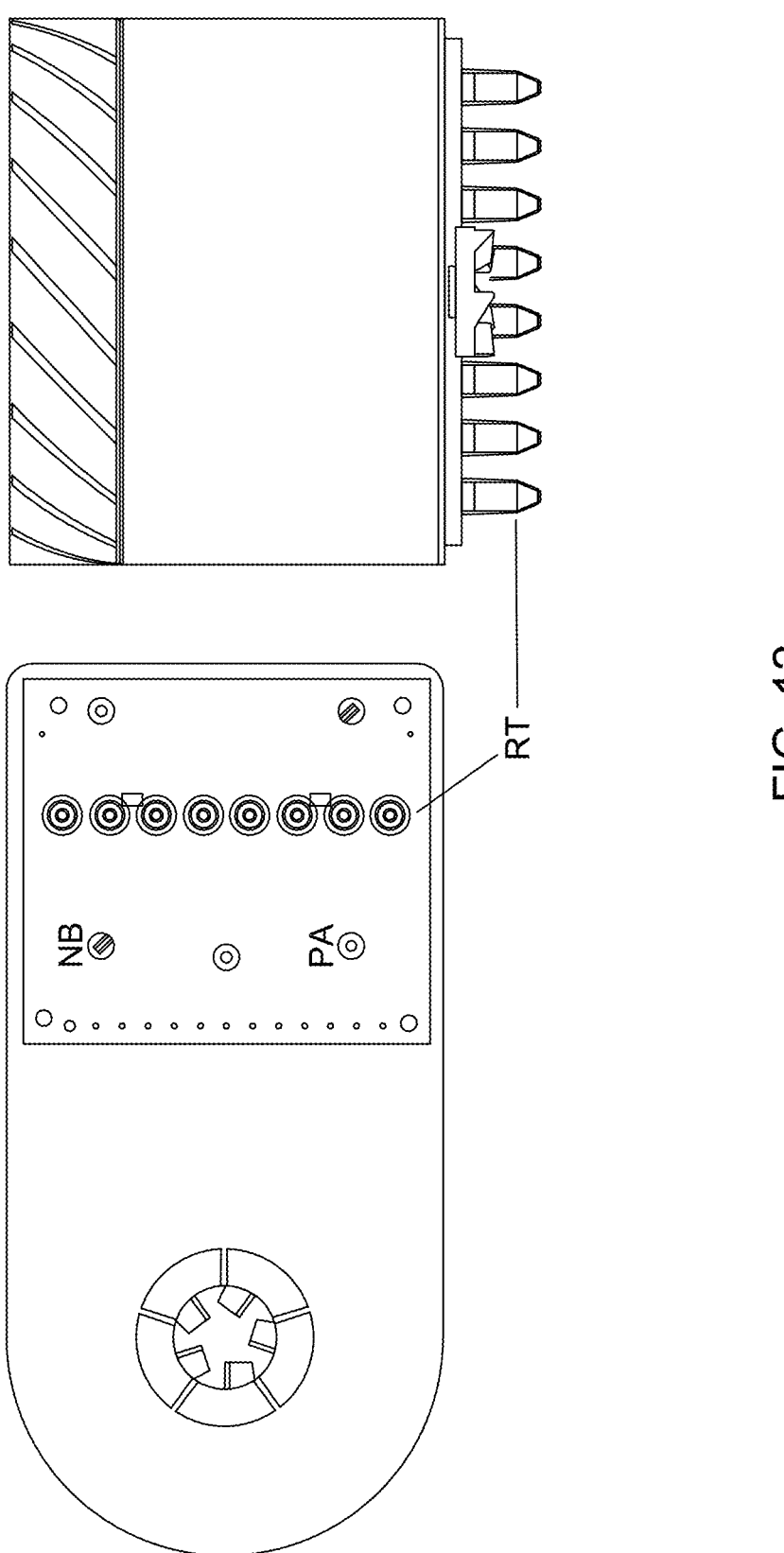

After filtration, the prepared analyte solution has pH over 13. These conditions are not compatible with the downstream enzymatic reaction. To neutralize the pH, a neutralization buffer containing 1-5 volumes of Tris-HCl 180 mM/EDTA 26 mM pH 8.0 is mixed together with the prepared analyte solution. In the capsule, this neutralization step is executed in a microfluidic chip. Inside the microfluidic chip (FIG. 12) diaphragm pumps mix the filtered prepared analyte (PA) with the neutralization buffer (NB) and then redistribute it inside reaction tubes (RT).

Reaction tubes contain all the necessary reactants for the analysis of DNA. For example, in a reaction for detection of a DNA of porcine origin described in detail in patent application EP3309154A1, reaction tubes contain two "Velcro" probes comprising two different nucleic acid sequences which are specific for pork target DNA (CAGCCCG-GAACCCTACTTGGCGATGATCAAATCTATAATG, SEQ ID NO: 3). Probe 1 (referred in EP3309154A1 as L') was used as an anchor and comprises a nucleic acid sequence of SEQ ID NO: 1 (CTTGGGATGAAC) that hybridizes to a part of target DNA sequence (part L). Probe 2 (referred in EP3309154A1 as R') was used as catalyst probe comprising a nucleic acid of SEQ ID NO: 2 (CTACTAGTTTAGAT) that hybridizes to a part of target DNA (part R) and was conjugated to a catalyst (Ru(bpy)2Phen). In presence of a reducing agent (100 mM ascorbic acid), porcine DNA in the reaction tube allows the transformation of a pro-fluorophore (described in patent EP3309154A1) into a fluorophore resulting in fluorescence signal in the solution.

In another example, the reaction tube contain primer and enzymes (i.e. Bst DNA polymerase) to amplify target DNA via PCR or isothermal amplification like LAMP. In these examples, fluorescence signal is generated by an intercalant (i.e. Evagreen) that becomes fluorescent once intercalated in double-stranded DNA obtained via polymerase chain reaction.

In the present invention, when the capsule is inserted inside the reader, the reaction tubes are in contact with a standard temperature-controlled fluorescence reader. Reaction tubes are then incubated at the desired temperature and the reaction is monitored through fluorescence during the whole reaction. Temperature and fluorescence data is recorded in a temporary memory.

EXAMPLE 4: UPLOADING PERFORMED MEASUREMENTS TO THE CERTIFICATION SERVER

The recorded data are written in a csv file and streamed through a MQTT server to the cloud where the data analysis is performed.

The raw csv file is structured to identify:
1. The data corresponding to the ID of the capsule, the ID of the reader, necessary timestamps and the nature of the sample for which the analysis was requested.
2. The raw data of the DNA amplification reactions from the separate reaction tubes.
3. The data used to validate the analysis itself. For example, the controls captured during the process, such as temperature, pressure of different pneumatic lines and position at a given time of the actuators present in the reader.

EXAMPLE 5: PERFORMING QUALITY CONTROLS TO VALIDATE THE CONFORMITY OF THE ANALYSIS

Figure 13:
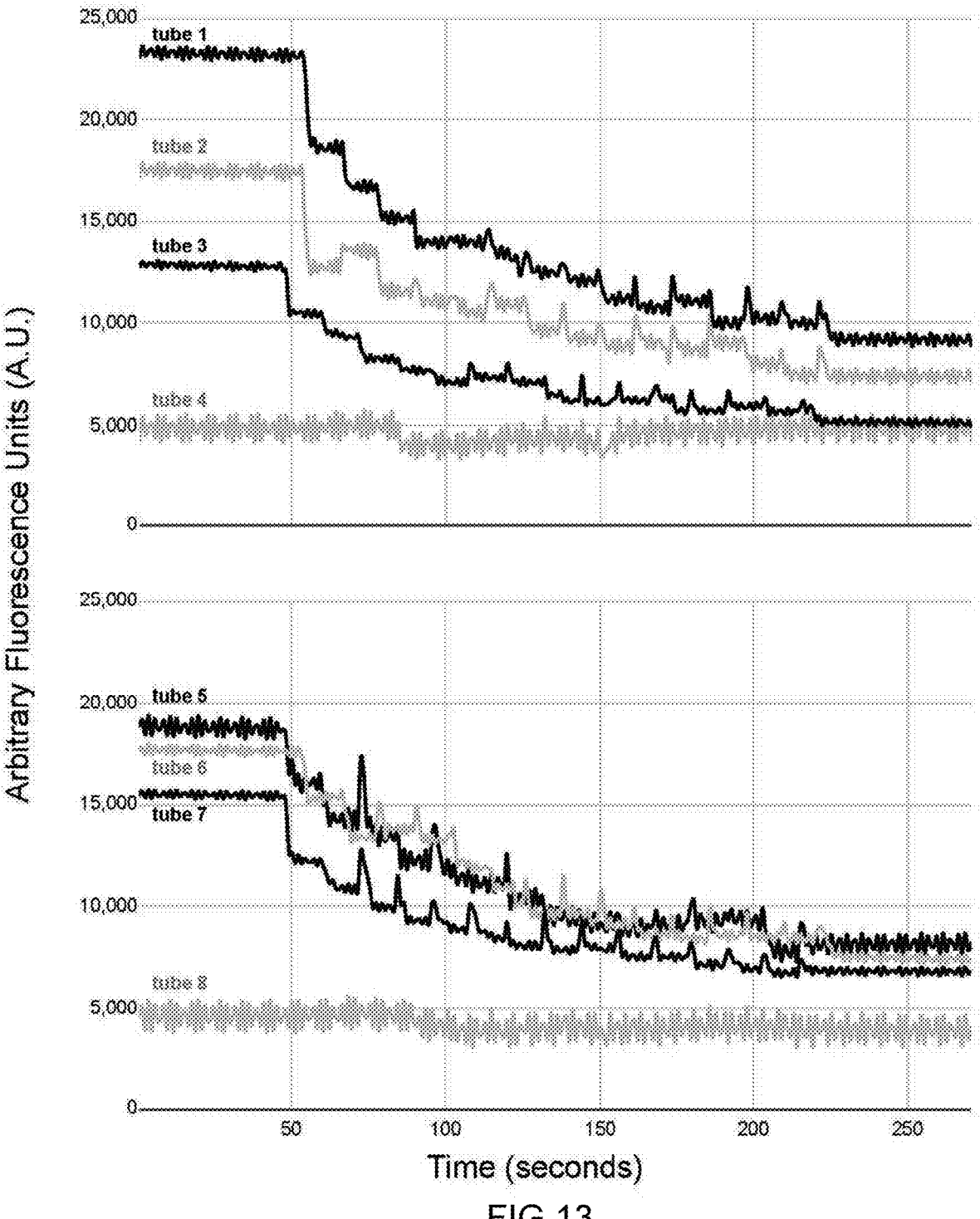
FIG. 13 is a graph showing the evolution of the fluorescence (Y axis, A.U) over time (X axis, seconds) on the 8 reaction tubes during reagent rehydration, in the food certification process example of FIGS. 9 to 12.

Various controls are put in place to control the conformity of the analysis, for example:
1. The torque in the blending chamber can be monitored to confirm that the homogenization is complete.
2. The pressure on the different pneumatic lines driving the fluidic chip is monitored with an independent and redundant array of pressure sensors. A routine then verifies that the valves have opened and closed with the correct timing to guarantee correct functioning of the chip.
3. A Probe Check Control is a simple check of the fluorescence level before the amplification reaction starts. Once the reaction tubes are filled, the fluorescence signal is measured and the values have to meet predefined acceptance criteria for compliance. The Probe Check Control enables to verify reagent rehydration, reaction tubes filling, primers integrity and green dye stability. FIG. 13 shows the evolution of the fluorescence (Y axis, A.U) over time (X axis, seconds) on the 8 tubes during reagent rehydration. The vertical lines represent the alternated injection of liquid in the reaction tubes which dilutes the fluorophore and results in a decrease of the fluorescent signal as expected.

Note: The lines are not superposed since the photodiodes have an automated calibration of the internal gain which offsets the curves.
4. A sample processing control composed of dehydrated cells or DNA from a different species is stored within the capsule and added to the blending chamber just before sample preparation, and detected with specific primers in a dedicated reaction tube. It controls the adequate processing of the sample, verifies enzyme integrity and monitors the presence of inhibitors in the amplification reaction. The amplification time needs to meet predefined acceptance criteria for compliance.

EXAMPLE 6: ANALYZING THE RESULTING MEASUREMENT, VERIFYING AND VALIDATING THE ANALYSIS PROTOCOL

On the certification server, the analysis of the raw data follows a defined algorithm typical of the analysis of real-time PCR amplification, for example double delta Ct method described by Livak, K. J. and Schmittgen, T. D., 2001. *Analysis of relative gene expression data using real-time quantitative PCR and the* 2—$\Delta\Delta CT$ method. methods. 25(4), pp. 402-408. The algorithm used and the validation is disclosed to the accreditation authorities.

Data about the process are analyzed once sent to the cloud to validate that every step went accordingly to the planned protocol. Redundant system are present to monitor the evolution of the pressure over time to validate the operation of the pneumatic chip.

EXAMPLE 7: EMITTING A CERTIFICATE OF ANALYSIS

A certificate of analysis is generated in the server, passes quality control steps and is sent to the customer as agreed in the service agreement (e.g. through a connection with the customer's ERP system).

Further preferred embodiments of the invention are defined in the following aspects:
1. Single-use capsule (3) for nucleic acid testing of a food sample, the capsule comprising
   a housing (4),
   a homogenizing chamber (12) in the housing for receiving a food sample,
   a blender (5) within the homogenizing chamber (2),
   one or more reagent containers (8) mounted in the housing, the one or more reagent containers containing reagents (9, 9a, 9b, 9c) for a DNA amplification process, optionally wherein the reagents (9, 9a, 9b, 9c) for a DNA amplification process are hermetically sealed in the one or more reagent containers (8) prior to use of the capsule, and
   one or more reaction chambers.
2. Single-use capsule of aspect 1, the homogenizing chamber being configured to accommodate at least 5 g, preferably at least 15 g and more preferably at least 25 g of the food sample.
3. Single-use capsule of any preceding aspect, the homogenizing chamber being configured to accommodate at most 100 g, preferably at most 150 g and more preferably at most 200 g of the food sample.
4. Single-use capsule of any preceding aspect, the homogenizing chamber having a volume of not less than 5 $cm^3$, preferably not less than 15 $cm^3$ and more preferably not less than 25 $cm^3$.

5. Single-use capsule of any preceding aspect, the homogenizing chamber having a volume of not more than 100 cm³, preferably not more than 150 cm³ and more preferably not more than 200 cm³.

6. Single-use capsule of any preceding aspect, further comprising a fluid distribution base (6) coupled to the housing for mixing and distributing the reagents and extracts of the food sample, preferably wherein:
the one or more reaction chambers are coupled to the fluid distribution base in an irremovable manner and/or a monolithically formed with the fluid distribution base; and/or
the fluid distribution base has liquid pumps (P1, P2, P3) and one or more pneumatic inlets couplable sealingly to one or more pneumatic outlets of a reader for operation of the liquid pumps.

7. Single-use capsule according to any preceding aspect, further comprising a fluid distribution base (6) coupled to the housing for mixing and distributing the reagents and extracts of the food sample wherein the fluid distribution base (6) comprises liquid pumps (P1, P2, P3) and fluid circuits therein for transport of liquid into one or more test tubes (7) and having one or more pneumatic inlets couplable sealingly to one or more pneumatic outlets of a reader for operation of the liquid pumps.

8. Single-use capsule of aspect 7, wherein the one or more test tubes form the one or more reaction chambers.

9. Single-use capsule of any preceding aspect, the fluid distribution base having fluid circuits therein for distributing the reagents and the extracts of the food sample to the one or more reaction chambers.

10. Single-use capsule of aspect 9, the fluid distribution base having one or more pumps for transferring the reagents and the extracts of the food sample in the fluid circuits.

11. Single-use capsule of aspect 9 or 10, the capsule further comprising one or more pneumatic inlets in communication with the fluid circuits for operation of the pumps, preferably the one or more pneumatic inlets being provided in the fluid distribution base.

12. Single-use capsule of any preceding aspect, the one or more pumps comprising a peristaltic pump, a membrane pump.

13. Single-use capsule of any of aspects 6-12, the capsule being configured such that fluid entering from the one or more pneumatic inlets is isolated from the food sample throughout the nucleic acid testing.

14. Single-use capsule of any preceding aspect, the fluid distribution base being irremovably coupled to the housing.

15. Single-use capsule of any preceding aspect, wherein all the reagents are integrally contained within the capsule and inaccessible to an operator without destruction of the capsule.

16. Single-use capsule according to any preceding aspect, wherein the reagents contained within the capsule include a lyophilized substance within the one or more reaction chambers (e.g. within the one or more test tubes) configured for producing a master-mix for specific DNA amplification.

17. Single-use capsule of any preceding aspect, a substance for producing a master-mix for specific DNA amplification is provided in the one or more reaction chambers.

18. Single-use capsule of aspect 17, the substance being resistant to at least one PCR inhibitor.

19. Single-use capsule of any of aspects 16-18, the substance comprising an enzyme such as Bst DNA polymerase, GspM DNA polymerase, Phi29 DNA polymerase.

20. Single-use capsule of any of aspects 16-19, the substance being contained in at least one lyophilized pellet.

21. Single-use capsule of any preceding aspect, the one or more reaction chambers containing primer and enzymes for amplifying a target DNA via PCR or isothermal amplification.

22. Single-use capsule of any preceding aspect, the blender being configured to be rotated by a blender motor to homogenize the food sample.

23. Single-use capsule of any preceding aspect, the blender comprising a pluggable coupling (20) for coupling to a complementary pluggable coupling of a motor of a reader.

24. Single-use capsule of any preceding aspect, the blender having one or more blades (18), preferably the one or more blades sealingly coupled to a pluggable coupling (20) for coupling to a complementary pluggable coupling of a motor of a reader.

25. Single-use capsule according to any preceding aspect, wherein the reagents include a lysis buffer contained within a flexible pouch (8a) within a storage chamber (10) of the capsule, preferably the storage chamber being connected via an inlet (24a) for coupling to a pneumatic system of a reader for controlled release of lysis buffer with homogenized food sample in the homogenizing chamber (12).

26. Single-use capsule of the preceding aspect, the pouch forming the hermetically sealed reagent container such that air does not enter into the pouch as the lysis buffer is consumed.

27. Single-use capsule according to any preceding aspect, wherein the reagents contained within the capsule further include a neutralization buffer and a resuspension buffer.

28. Single-use capsule according to any preceding aspect, wherein the homogenizing chamber (12) of the capsule comprises a lid or cover (28) comprising fixing means that are preferably irreversible without damage to the capsule once closed.

29. Single-use capsule of any preceding aspect, the capsule comprising a lid (28) and an irreversible locking mechanism for the lid such that once the homogenizing chamber is closed by the lid, the lid may not be removed without destruction of the capsule and/or the lid.

30. Single-use capsule according to any preceding aspect, comprising one or more perforators (34) for perforating said one or more reagent containers, preferably wherein the capsule comprises perforators (34) and a movable support (17) configured to perforate one or more said reagent containers by displacement of said movable support either when the capsule is positioned in a reader by a mechanical clamping process, or by means of an automated electrical or pneumatic displacement of the movable support operated by a reader at the start of a testing procedure.

31. Single-use capsule of any preceding aspect, the one or more reagent containers each containing at least 0.5 mL, preferably 1 mL of the reagents.

32. Single-use capsule of any preceding aspect, the one or more reagent containers each containing at most 1 L, preferably 0.5 L and more preferably 0.25 L of the reagents.

33. Food certificate system (1) comprising
a certificate generation server (102),
at least one reader (2) comprising a control unit configured to operate a DNA test procedure and communicate with the certificate generation server (102) via a global computer network (100), and
a single-use capsule (3), preferably according to any of the preceding aspects, insertable in the reader (2) in a detection position for analyzing DNA characteristics of the food sample (104) contained in the capsule (3) and transmission of the DNA measurement results to the certificate generation server (102).

34. System according to aspect 33, wherein the reader comprises a reader base (36) and a clamping mechanism for clamping the capsule in a clamped position in which a pneumatic circuit of the reader is sealingly coupled to one or more pneumatic inlets of the capsule (3) and a blender motor of the reader is pluggably coupled to the blender (5) mounted in the housing (4) of the capsule (3).

35. System according to aspect 33 or 34, wherein the reader includes a DNA testing system including a fluorometer measuring fluorescent light emitted by sample liquid in the one or more reaction chambers, preferably the one or more reaction chambers comprising one or more test tubes, wherein the DNA testing system preferably is included in a reader base (6).

36. System according to any of aspects 33-35, wherein the reader base comprises a block having wells therein receiving the reaction chambers of the capsule therein.

37. System according to any of aspects 34-36, wherein the reader base comprises heating and cooling elements for DNA amplification and for stopping or slowing the DNA amplification process.

38. System according to any of aspects 33-37, wherein a plurality of readers in different locations are connected to the certificate generation server.

39. System of any of aspects 33-38, wherein the reader comprises a sensor for monitoring a degree of homogeneity of the food sample in the homogenizing chamber, preferably the sensor being a torque meter or a camera.

40. System of any of aspects 34-39, wherein the reader comprises a torque meter measuring a torque of the blender motor.

41. Method of testing a food sample using a system according to any of aspects 33-40, wherein the certificate generation server controls the operation of the reader remotely, the reader performing an automated testing process without the intervention from an operator once the capsule is inserted in the reader and the testing process started.

42. Method according to aspect 41, wherein the method comprises performing DNA testing of the food samples and issuance of a certificate, and preferably comprises the steps of inserting the food sample in the homogenizing chamber of the capsule, isolating the food sample into the capsule, inserting the capsule in the reader, starting the DNA testing procedure and transmission of the measurement results from the reader to the remote certificate generation server via the global computer network, wherein the testing procedure, transmission of results and analysis may be controlled by the remote server.

43. Method of aspect 41 or 42, the food sample being tested comprises processed foods, unprocessed plant or animal material, or semi-processed plant or animal material, preferably the processed foods, the unprocessed plant or animal material and the semi-processed plant or animal material not being subject to any further pre-processing.

What we claim is:

1. A single-use capsule for nucleic acid testing of a food sample, the capsule comprising
a housing,
a homogenizing chamber in the housing for receiving a food sample,
a blender within the homogenizing chamber, the blender comprising a pluggable coupling for coupling to a complementary pluggable coupling of a motor of a reader,
reagent containers mounted in the housing, the reagent containers containing reagents for a DNA amplification process hermetically sealed therein prior to use of the capsule,
a fluid distribution base having liquid pumps and pneumatic inlets couplable sealingly to pneumatic outlets of a reader for operation of the liquid pumps, the fluid distribution base coupled to the housing for mixing and distributing the reagents and extracts of the food sample, and
reaction chambers coupled to the fluid distribution base in an irremovable manner.

2. The single-use capsule according to claim 1 wherein the homogenizing chamber is configured to accommodate at least 25 g of the food sample.

3. The single-use capsule of claim 1, the homogenizing chamber having a volume of not less than 25 cm$^3$.

4. The single-use capsule of claim 1, the fluid distribution base having fluid circuits therein for distributing the reagents and the extracts of the food sample to the reaction chamber.

5. The single-use capsule of claim 1, wherein the capsule is configured such that fluid entering from the pneumatic inlets is isolated from the food sample throughout the nucleic acid testing.

6. The single-use capsule of claim 1, wherein the fluid distribution base is irremovably coupled to the housing.

7. The single-use capsule of claim 1, wherein all the reagents are integrally contained within the capsule and inaccessible to an operator without destruction of the capsule.

8. The single-use capsule according to claim 1, wherein a substance for producing a master-mix for specific DNA amplification is provided in the reaction chamber.

9. The single-use capsule of claim 8, wherein the substance is resistant to at least one PCR inhibitor.

10. The single-use capsule according to claim 1, wherein the reagents include a lysis buffer contained within a flexible pouch within a storage chamber of the capsule.

11. The single-use capsule of claim 10, wherein the pouch forms the hermetically sealed reagent container such that air does not enter into the pouch as the lysis buffer is consumed.

12. The single-use capsule of claim 10, wherein the storage chamber is connected via an inlet for coupling to a pneumatic system of a reader for controlled release of lysis buffer with homogenized food sample in the homogenizing chamber.

13. The single-use capsule of claim 1, wherein the capsule comprises a lid and an irreversible locking mechanism for the lid such that once the homogenizing chamber is closed by the lid, the lid may not be removed without destruction of the capsule.

14. The single-use capsule according to claim 1, further comprising perforators and a movable support configured to perforate one or more said reagent containers by displacement of said movable support either when the capsule is positioned in a reader by a mechanical clamping process, or by means of an automated electrical or pneumatic displacement of the movable support operated by a reader at the start of a testing procedure.

15. A food certificate system comprising:
a certificate generation server,
at least one reader comprising a control unit configured to operate a DNA test procedure and communicate with the certificate generation server via a global computer network, and
a single-use capsule according to any of the preceding claims insertable in the reader in a detection position for analyzing DNA characteristics of the food sample contained in the capsule and transmission of the DNA measurement results to the certificate generation server.

16. The system of claim 15, wherein the reader comprises a sensor for monitoring a degree of homogeneity of the food sample in the homogenizing chamber.

17. The system of claim 16, wherein the sensor is a torque meter or a camera.

18. A method of testing a food sample using a system according to claim 15, wherein the certificate generation server controls the operation of the reader remotely, the reader performing an automated testing process without the intervention from an operator once the capsule is inserted in the reader and the testing process started.

19. The method of claim 18, wherein the method comprises performing DNA testing of the food samples and issuance of a certificate, and comprises the steps of inserting the food sample in the homogenizing chamber of the capsule, isolating the food sample into the capsule, inserting the capsule in a reader, starting the DNA testing procedure and transmission of the measurement results from the reader to the remote certificate generation server via the global computer network, wherein the testing procedure, transmission of results and analysis may be controlled by the remote server.

20. The method of claim 18, wherein the food sample being tested comprises processed foods, unprocessed plant or animal material, or semi-processed plant or animal material, wherein the processed foods, the unprocessed plant or animal material and the semi-processed plant or animal material is not subject to any further pre-processing.

* * * * *